United States Patent
Oliphant et al.

(10) Patent No.: US 9,567,639 B2
(45) Date of Patent: Feb. 14, 2017

(54) DETECTION OF TARGET NUCLEIC ACIDS USING HYBRIDIZATION

(71) Applicant: Ariosa Diagnostics, Inc., San Jose, CA (US)

(72) Inventors: Arnold Oliphant, San Jose, CA (US); Jacob Zahn, San Jose, CA (US); Kara Juneau, San Jose, CA (US); Patrick Bogard, San Jose, CA (US); Stephanie Huang, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 0 days.

(21) Appl. No.: 14/453,396

(22) Filed: Aug. 6, 2014

(65) Prior Publication Data

US 2014/0349859 A1    Nov. 27, 2014

Related U.S. Application Data

(63) Continuation of application No. 14/450,144, filed on Aug. 1, 2014, which is a continuation-in-part of application No. 13/013,732, filed on Jan. 25, 2011, and a continuation-in-part of application No. 13/205,490, filed on Aug. 8, 2011, and a continuation-in-part of application No. 13/205,603, filed on Aug. 8, 2011, said application No. 13/205,490 is a continuation-in-part of application No. 13/316,154, filed on Dec. 9, 2011, now abandoned.

(60) Provisional application No. 61/371,605, filed on Aug. 6, 2010, provisional application No. 61/436,135, filed on Jan. 25, 2011.

(51) Int. Cl.
C12Q 1/68        (2006.01)
C12P 19/34       (2006.01)
G06F 19/20       (2011.01)

(52) U.S. Cl.
CPC .......... *C12Q 1/6883* (2013.01); *C12Q 1/6827* (2013.01); *C12Q 1/6837* (2013.01); *C12Q 1/6862* (2013.01); *G06F 19/20* (2013.01); *C12Q 2600/166* (2013.01)

(58) Field of Classification Search
CPC ..................... C12Q 1/6862; C12Q 2600/166
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |

(Continued)

FOREIGN PATENT DOCUMENTS

| | | |
|---|---|---|
| GB | 2299166 | 9/1996 |
| WO | WO87/06270 | 10/1987 |

(Continued)

OTHER PUBLICATIONS

Shen et al. BMC Genetics. 2008. 9:27.*

(Continued)

*Primary Examiner* — Joseph G Dauner
(74) *Attorney, Agent, or Firm* — Mintz Levin Cohn Ferris Glovsky and Popeo, P.C.

(57) ABSTRACT

The present invention provides detection systems and methods for detection of loci and genomic regions in a sample, including mixed samples, using hybridization to an array.

23 Claims, 14 Drawing Sheets

(56) References Cited

U.S. PATENT DOCUMENTS

| | | |
|---|---|---|
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,316,229 B1 | 11/2001 | Lizardi |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Dennis et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,296,076 B2 | 10/2012 | Fan et al. |
| 8,318,430 B2 | 11/2012 | Chuu et al. |
| 2001/0051341 A1 | 12/2001 | Lo et al. |
| 2002/0045176 A1 | 4/2002 | Lo et al. |
| 2002/0132241 A1 | 9/2002 | Fan et al. |
| 2002/0160361 A1 | 10/2002 | Loehrlein et al. |
| 2003/0003459 A1 | 1/2003 | Stahl |
| 2003/0044388 A1 | 3/2003 | Dennis et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0137470 A1* | 7/2004 | Dhallan ........................... 435/6 |
| 2004/0203037 A1 | 10/2004 | Lo et al. |
| 2004/0214175 A9 | 10/2004 | McKernan et al. |
| 2005/0095618 A1 | 5/2005 | Tsuio et al. |
| 2005/0100939 A1 | 5/2005 | Namsaraev et al. |
| 2005/0191656 A1 | 9/2005 | Drmanac et al. |
| 2006/0121452 A1 | 6/2006 | Dhallan |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0090239 A1 | 4/2008 | Shoemaker et al. |
| 2008/0096766 A1 | 4/2008 | Lee |
| 2008/0138809 A1 | 6/2008 | Kapur et al. |
| 2008/0206749 A1 | 8/2008 | Lo et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |

(56) References Cited

U.S. PATENT DOCUMENTS

| | | |
|---|---|---|
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0040859 A1 | 2/2012 | Sparks et al. |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 7/2012 | Hixson |
| 2012/0191358 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava |
| 2013/0288244 A1 | 10/2013 | Deciu et al. |
| 2014/0024538 A1 | 1/2014 | Zahn et al. |

FOREIGN PATENT DOCUMENTS

| | | |
|---|---|---|
| WO | WO90/06995 | 6/1990 |
| WO | WO99/47964 | 9/1999 |
| WO | WO-00/04193 A1 | 1/2000 |
| WO | WO03/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO-2011/066476 A1 | 6/2011 |
| WO | WO-2011/066476 A8 | 6/2011 |
| WO | WO2011/090556 | 7/2011 |
| WO | WO2011/090557 | 7/2011 |
| WO | WO2011/090558 | 7/2011 |
| WO | WO-2012/088456 A2 | 6/2012 |
| WO | WO-2012/088456 A3 | 6/2012 |
| WO | WO-2013/192292 A1 | 12/2013 |
| WO | WO-2016/018986 A1 | 2/2016 |

OTHER PUBLICATIONS

Shen et al. Mutation Research. 2005. 573: 70-82.*

Sparks, et al., "Selective analysis of cell-free DNA in maternal blood for evaluation of fetal trisomy", Prenatal Diagnosis, 32:1-7 (2012).

Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.

Stroun, et al., "Neoplastic Characteristics of the DNA Found in the Plasma of Cancer Patients", Oncology, 46: 318-322 (1989).

Stroun, et al., "Isolation and Characterization of DNA from the Plasma of Cancer Patients", Eur. J. Cancer Clin. Oncol., 23(6)707-12 (1987).

Stroun, et al., "Circulating Nulceic Acids in Higher Organisms", Rev. Cytol. 51:1-48 (1977).

Stroun, et al., The Origin and Mechanism of Circulating DNA, Annals New York Academy of Sciences, 906:161-68 (2000).

Sullivan, et al., "Evidence for Structural Heterogeneity from Molecular Cytogenetic Analysis of Dicentric Robertsonian Translocations", Am. J. Hum. Genet., 59:167-75 (1996).

Tagle, et al., "An optimized Alu-PCR primer pair for human-specific amplification of YACs and somatic cells hybrids", Human Molecular Genetics, 1(2):121-22 (1992).

Tomilin, et al., "Mechanisms of Chromosome Destabilization in Human Cells", Sov. Sci. Rev. D. Physiochem. Biol., 10:39-89 (1992).

Tong, et al., "Noninvasive prenatal detection of fetal trisomy 18 by epigenetic allelic ratio analysis in maternal plasma: theoretical and empirical considerations", Clin Chem, 52:2194-202 (2006).

Tsui, et al., "Systematic microarray-based identification of placental mRNA in maternal plasma: towards non-invasive prenatal gene expression profiling", J. Med Genet, 41:461-67 (2004).

Tsui, et al., "Noninvasive prenatal diagnosis of hemophilia by microfluidics digital PCR analysis of maternal plasma DNA", Blood, 117:3684=91 (2011).

Ulbright, "Germ cell tumors of the gonads: a selective review emphasizing problems in differential diagnosis, newly appreciated, and controversial issues," Modern Pathology, 18:S61-S79 (2005).

Vasioukhin, et al., "Point mutations in the N-ras gene in the blood plasma DNA of patients with myelodysplastic cyndrome or acute myelogenous leukaemia", British J. of Haematology, 86:774-79 (1994).

Vogelstein, et al., "Digital PCR", PNAS USA, 96:9236-41 (1999).

Wachtel, et al., "Fetal cells in the maternal circulation: Isolation by multiparameter flow cytometry and confirmation by polymerase chain reaction", Human Reprod., 6(10):1466-69 (1991).

Wald, et al., "Maternal serum screening for Down's syndrome in early pregnancy", BMJ, 297:883-87 (1988).

Wald, et al., "Antenatal maternal serum screening for Down's syndrome: results of a demonstration project", BMJ, 305(6850):391-94 (1992).

Walker, et al., "Human DNA quantitation using Alu element-based polymerase chain reaction", Analytical Biochem., 315:122-28 (2003).

Wang, et al., "PennCNV: An integrated hidden Markov model designed for high-resolution copy number variation detection in whole-genome SNP genotyping data", Genome Res., 17:1665-74 (2007).

Ward, et al., "Reactivities of serotyping monoclonal antibodies with culture-adapted human rotaviruses", J. Clin. Microbiol. 29(3):422-25 (1991).

Winsor, et al., "Maternal Cell Contamination in Uncultured Amniotic Fluid", Prenatal Diagnosis, 16:49-54 (1996).

Witt, et al., "An improved, non-isotopic method of screening cells from patients with abnormalities of sexual differentiation for Y chromosomal DNA content", J. Med. Genet., 30:304-07 (1993).

(56) References Cited

OTHER PUBLICATIONS

Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Search Report Received on Oct. 15, 2012 for (PCT/US2011/046981).
Search Report Received on Jan. 20, 2012 for (PCT/US2012/21955).
Search Report Received on May 2, 2012 for PCT/US2011/046935).
Search Report Received on May 10, 2012 for (PCT/US2012/026754).
Search Report Received on May 11, 2012 for (PCT/US2012/022261).
Search Report Received on Feb. 21, 2013 for (PCT/US2011/046963), entire document.
Search Report Received on Apr. 19, 2013 for (PCT/US2012/70177), entire document.
Office Action Received on Apr. 15, 2013 for U.S. Appl. No. 13/356,133, (inventor A. Oliphant, filed Jan. 23, 2012), entire document.
Office Action Received on May 17, 2013 for U.S. Appl. No. 13/356,575, (inventor A. Oliphant, filed Jan. 23, 2012), entire document.
Office Action Received on Apr. 5, 2013 for U.S. Appl. No. 13/689,206, (inventor A. Oliphant, filed Nov. 39, 2012).
Final Office Action Received on Jul. 8, 2013 for U.S. Appl. No. 13/689,206, (inventor A. Oliphant, filed Nov. 39, 2012), entire document.
Office Action Received on Jul. 5, 2012 for U.S. Appl. No. 13/013,732, (inventor A. Oliphant, filed Jun. 25, 2011).
Office Action Received on Dec. 7, 2012 for U.S. Appl. No. 13/013,732, (inventor A. Oliphant, filed Jun. 25, 2011), entire document.
Office Action Received on Apr. 11, 2013 for U.S. Appl. No. 13/013,732, (inventor A. Oliphant, filed Jun. 25, 2011), entire document.
Office Action Received on May 13, 2013 for U.S. Appl. No. 13/407,978, (inventor K. Song, filed Feb. 29, 2012), entire document.
Office Action Received on Jul. 8, 2013 for U.S. Appl. No. 13/205,490, (inventor A. Sparks, filed Aug. 8, 2011), entire document.
Office Action Received on Mar. 28, 2013 for U.S. Appl. No. 13/687,169, (inventor A. Sparks, filed Nov. 28, 2012), entire document.
Office Action Received on Feb. 28, 2013 for U.S. Appl. No. 13/205,570, (inventor A. Sparks, filed Aug. 8, 2011), entire document.
Office Action Received on Mar. 14, 2013 for U.S. Appl. No. 13/687,025, (inventor A. Sparks, filed Nov. 28, 2012), entire document.
Office Action Received on May 10, 2012 for U.S. Appl. No. 13/293,419, (inventor A. Sparks, filed Nov. 10, 2011), entire document.
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Enrich, et al., "Noninvasive detection of fetal trisomy 21 by sequencing of fetal DNA in maternal blood: a study in a clinical setting", AM J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie, et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostate Carcinoma Clinical Implications", J. of Clin. Oncology, 13(5):1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874-(1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).

(56) References Cited

OTHER PUBLICATIONS

Hosny, et al., "TP53 mutations in circulating fee DNA from Egyptian patients with non-Hodgkin's lymphoma", Cancer Lett., 275(2):234-39 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis ofgenetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Abadia-Molina, et al., "Immune phenotype and cytotoxic activity of lymploycytes from human term decidua against trophoblast", J. of Reproductive Immunology, n31:109-23 (1996).
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).

Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.
Arnheim, et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neo-natal human leucocytes expressing natural killer cell-associated antigen", Immunology and Cell Biology (71:535-42 (1993).
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Natl Cancer Inst., 97(9):643-55 (2005).
Cicuttini and Boyd, "Hemopoietic and Lymphoid Progenitro Cells in Human Umbilical Cord Blood", Developmental Immunology, 4:1-11 (1994).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the *maspin* gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).

(56) References Cited

OTHER PUBLICATIONS

Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. Of Clinical Oncology, 12(3): 475-82 (1994).
Dear, et al., "A High-Resolution Metric HAPPY Map of Human Chromosome 14" Genmoics, 48 232-41 (1998).
Dennin, "DNA of Free and Complexed Origin in Human Plasma: Concentration and Length Distribution", Klin Wochenschr., 57:451-56 (1979).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).

Margulies, et al., "Genome sequencing in microfabricated high-density picolitre reactors", Nature, 437(15):376-80 and errata (2005).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Mulcahy, et al., "Plasma DNA K-rase Mutations in Patients with Gastrointestinal Malignancies," Annals New York Academy of Sciences, 25-28.
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Oei, et al., "Clusters of regulatory signals for RNA polymerase II transcription associated with Alu family repeats and CpG islands in human promoters", Genomics, 83:873-83 (2004).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Paolella, et al., "The Alu family repeat promoter has a tRNA-like bipartite structure", Embo J., 2(5):691-96 (1983).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., *Pathologic Basis of Disease 5th Ed.*, Chapter 23, pp. 1071-1088 (1994).
Ronaghi, et al., "A Sequencing Method Based on Real_Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Shendure, et al., "Accurate Multiplex Polony Sequencing of an Evolved Bacterial Genome", Science, 309:1728-32 (2005).

(56) References Cited

OTHER PUBLICATIONS

Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Desease", Cancer, 51:2116-20 (1983).
Simpson and Elias, "Isolating Fetal Cells from Maternal Blood", JAMA, 270(19):2357-61 (1993).
Simpson, et al., "Isolating Fetal Cells in Maternal Circulation for Prenatal Diagnosis", Prenatal Diagnosis, 14:1229-42 (1994).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Smith, et al., "Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Final Office Action Received on Oct. 12, 2012 for U.S. Appl. No. 13/293,419, (inventor A. Sparks, filed Nov. 10, 2011), entire document.
Advisory Action Received on Jan. 29, 2013 for U.S. Appl. No. 13/293,419, (inventor A. Sparks, filed Nov. 10, 2011), entire document.
Office Action Received on Feb. 28, 2013 for U.S. Appl. No. 13/245,133, (inventor A. Oliphant, filed Sep. 26, 2011), entire document.
Office Action Received on Jun. 13, 2013 for U.S. Appl. No. 13/316,154, (inventor A. Oliphant, filed Dec. 9, 2011), entire document.
Office Action Received on Jun. 13, 2013 for U.S. Appl. No. 13/338,963, (inventor A. Oliphant, filed Dec. 28, 2011), entire document.
Office Action Received on Feb. 15, 2013 for U.S. Appl. No. 13/689,417, (inventor A. Oliphant, filed Nov. 29, 2012), entire document.
Bianchi, et al., "Large Amounts of Cell-free DNAS Are Present in Amniotic Fluid", Clin. Chem., 47(10) 1867-69 (2001).
Centre for Genomics Education, "Changes to Chromosome Structure—Translocations", The Australasian Genetics Resource Book, www.genetics.com, pp. 1-5 (2007).
Chiu, et al., "Non-invasive prenatal diagnosis by single molecule counting technologies", Trends in Genomics, 25(7):324-31 (2009).

Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action Received on Oct. 31, 2013 for U.S. Appl. No. 13/356,575, filed Jan. 23, 2012, inventor Oliphant, entire document.
Office Action Received on Jun. 25, 2014 for U.S. Appl. No. 13/689,206, filed Nov. 29, 2012, inventor Oliphant, entire document.
Office Action Received on Feb. 11, 2014 for U.S. Appl. No. 13/689,206, filed Nov. 29, 2012, inventor Oliphant, entire document.
Office Action Received on Jun. 26, 2014 for U.S. Appl. No. 13/356,133, filed Jan. 23, 2012, inventor Oliphant, entire document.
Office Action Received on Oct. 18, 2013 for U.S. Appl. No. 13/356,133, filed Jan. 23, 2012, inventor Oliphant, entire document.
Office Action Received on Jul. 31, 2013 for U.S. Appl. No. 13/013,732, filed Jun. 25, 2011, inventor Oliphant, entire document.
Office Action Received on Apr. 14, 2014 for U.S. Appl. No. 13/013,732, filed Jun. 25, 2011, inventor Oliphant, entire document.
Office Action Received on Feb. 11, 2014 for U.S. Appl. No. 13/405,839, filed Feb. 27, 2012, inventor Oliphant, entire document.
Office Action Received on Oct. 25, 2013 for U.S. Appl. No. 13/407,978, filed Feb. 29, 2012, inventor Song, entire document.
Office Action Received on Jul. 30, 2014 for U.S. Appl. No. 13/407,978, filed Feb. 29, 2012, inventor Song, entire document.
Office Action Received on Jan. 31, 2014 for U.S. Appl. No. 13/605,505, filed Sep. 6, 2012, inventor Struble, entire document.
Office Action Received on Aug. 8, 2013 for U.S. Appl. No. 13/605,505, filed Sep. 6, 2012, inventor Struble, entire document.
Office Action Received on Aug. 30, 2013 for U.S. Appl. No. 13/687,169, filed Nov. 28, 2012, inventor Sparks, entire document.
Office Action Received on May 8, 2014 for U.S. Appl. No. 13/687,169, filed Nov. 28, 2012, inventor Sparks, entire document.
Office Action Received on Dec. 10, 2013 for U.S. Appl. No. 13/205,490, filed Aug. 8, 2011, inventor Sparks, entire document.
Office Action Received on Jul. 8, 2013 for U.S. Appl. No. 13/205,490, filed Aug. 8, 2011, inventor Sparks, entire document.
Office Action Received on Oct. 2, 2013 for U.S. Appl. No. 13/687,025, filed Nov. 28, 2012, inventor Sparks, entire document.
Office Action Received on Jul. 16, 2014 for U.S. Appl. No. 13/687,025, filed Nov. 28, 2011, inventor Sparks, entire document.
Office Action Received on Aug. 30, 2013 for U.S. Appl. No. 13/205,570, filed Aug. 8, 2011, inventor Sparks, entire document.
Office Action Received on May 8, 2014 for U.S. Appl. No. 13/205,570, filed Aug. 8, 2011, inventor Sparks, entire document.
Office Action Received on Jul. 14, 2014 for U.S. Appl. No. 13/293,419, filed Nov. 10, 2011, Sparks, entire document.
Office Action Received on Jun. 26, 2014 for U.S. Appl. No. 13/205,603, filed Aug. 8, 2011, inventor Sparks, entire document.
Office Action Received on Dec. 30, 2013 for U.S. Appl. No. 13/205,603, filed Aug. 8, 2011, inventor Sparks, entire document.
Office Action Received on Dec. 11, 2013 for U.S. Appl. No. 13/274,309, filed Oct. 15, 2011, inventor Struble, entire document.

(56) References Cited

OTHER PUBLICATIONS

Office Action Received on Aug. 30, 2013 for U.S. Appl. No. 13/245,133, filed Sep. 26, 2011, inventor Oliphant, entire document.
Office Action Received on Feb. 28, 2013 for U.S. Appl. No. 13/245,133, filed Sep. 26, 2011, inventor Oliphant, entire document.
Office Action Received on May 8, 2014 for U.S. Appl. No. 13/245,133, filed Sep. 26, 2011, inventor Oliphant, entire document.
Office Action Received on May 12, 2014 for U.S. Appl. No. 13/689,417, filed Nov. 29, 2012, inventor Oliphant, entire document.
Office Action Received on Oct. 31, 2013, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US2012/026754, entire document.
Search Report dated Nov. 15, 2013 for PCT/US2013/51310, entire document.
Search Report dated May 14, 2013 for PCT/US2014/17092, entire document.
Avent, N.D. (2008). "RHD genotyping from maternal plasma: guidelines and technical challenges," *Methods in Molecular Biology* 444:185-201.
Final Office Action mailed on Jul. 31, 2013, for U.S. Appl. No. 13/013,732, filed Jan. 25, 2011, 23 pages.
Final Office Action mailed on Nov. 14, 2014, for U.S. Appl. No. 13/013,732, filed Jan. 25, 2011, 39 pages.
Final Office Action mailed on Dec. 18, 2014 for U.S. Appl. No. 13/293,419, filed Nov. 10, 2011, 31 pages.
Final Office Action mailed on Mar. 7, 2016, for U.S. Appl. No. 13/013,732, filed Jan. 25, 2011, 48 pages.
Hardenbol, P. et al. (Jun. 2003, e-published May 5, 2003). "Multiplexed genotyping with sequence-tagged molecular inversion probes," *Nat Biotechnol* 21(6):673-678.
Jiang, F. et al. (Dec. 1, 2012). "Noninvasive Fetal Trisomy (NIFTY) test: an advanced noninvasive prenatal diagnosis methodology for fetal autosomal and sex chromosomal aneuploidies," *BMC Med Genomics* 5:57.
Lapaire, O. et al. (Mar. 2007, e-published Jan. 26, 2007). "Cell-Free DNA in Amniotic Fluid: Unique Fragmentation Signatures in Euploid and Aneuploid Fetuses," *Clinical Chem* 53(3):405-411.
Nicolaides, K.H. et al. (Jun. 2013, e-published Apr. 24, 2013). "Validation of targeted sequencing of single-nucleotide polymorphisms for non-invasive prenatal detection of aneuploidy of chromosomes 13, 18, 21, X and Y," *Prenatal Diagnosis* 33(6):575-579.
Non-Final Office Action mailed on Apr. 14, 2014, for U.S. Appl. No. 13/013,732, filed Jan. 25, 2011, 28 pages.
Non-Final Office Action mailed on Jul. 15, 2015, for U.S. Appl. No. 13/013,732, filed Jan. 25, 2011, 32 pages.
Non-Final Office Action mailed on Nov. 17, 2015 for U.S. Appl. No. 13/293,419, filed Nov. 10, 2011, 25 pages.
Palomaki, G.E. et al. (Mar. 2012, e-published Feb. 2, 2012). "DNA sequencing of maternal plasma reliably identifies trisomy 18 and trisomy 13 as well as Down syndrome: an international collaborative study," *Genet Med* 14(3):296-305.
International Search Report mailed on Aug. 12, 2014 for PCT/US2013/075683, filed on Dec. 17, 2013, 5 pages.
International Search Report mailed on Aug. 13, 2012 for PCT/US2011/046976, filed on Aug. 8, 2011, 6 pages.
U.S. National Library of Medicine. (Jan. 2013). Genetics Home Reference—ATM serine/threonine kinase. Located at <https://ghr.nlm.nih.gov/gene/ATM>, last visited Jun. 13, 2013, 4 pages.

* cited by examiner

DETECTION OF TARGET NUCLEIC ACIDS USING HYBRIDIZATION

CROSS-REFERENCE TO RELATED APPLICATIONS

The present application is a continuation of U.S. Ser. No. 14/450,144 filed Aug. 1, 2014, which is a continuation-in-part of U.S. Ser. No. 13/013,732, filed Jan. 25, 2011; U.S. Ser. No. 13/205,490, filed Aug. 8, 2011; and, U.S. Ser. No. 13/205,603, filed Aug. 8, 2011; all of which claim priority to U.S. Ser. No. 61/371,605, filed Aug. 6, 2010.

U.S. Ser. No. 13/205,490, filed Aug. 8, 2011, is a continuation-in-part of Ser. No. 13/013,732, filed Jan. 25, 2011; which claims priority to U.S. Ser. No. 61/371,605, filed Aug. 6, 2010.

U.S. Ser. No. 13/205,603, filed Aug. 8, 2011, is a continuation-in-part of Ser. No. 13/013,732, filed Jan. 25, 2011; which claims priority to U.S. Ser. No. 61/371,605, filed Aug. 6, 2010.

U.S. Ser. No. 13/013,732, filed Jan. 25, 2011 claims priority to U.S. Ser. No. 61/371,605, filed Aug. 6, 2010.

U.S. Ser. No. 14/450,144 is a continuation-in-part of Ser. No. 13/316,154, filed Dec. 9, 2011, which claims priority to U.S. Ser. No. 61/436,135, filed Jan. 25, 2011.

Each of the above references are incorporated by reference.

FIELD OF THE INVENTION

This invention relates to detection of target genomic regions from samples.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including pathologies caused by chromosomal aneuploidy (e.g., Down syndrome), germline mutations in specific genes (e.g., sickle cell anemia), and pathologies caused by somatic mutations (e.g., cancer). Diagnostic methods for determining genetic anomalies have become standard techniques for identifying specific diseases and disorders, as well as providing valuable information on disease source and treatment options.

Copy number variations (CNVs) are alterations of genomic DNA that correspond to specific regions of the genome—including entire chromosomes—that have been deleted or duplicated. CNVs can be caused by genomic rearrangements such as deletions, duplications, inversions, and translocations. CNVs have been associated with various forms of cancer (Cappuzzo F, Hirsch, et al. (2005) *J Natl Cancer Inst.*, 97(9):643-55), neurological disorders, including autism (Sebat, J., et al. (2007) *Science* 316(5823):445-9), and schizophrenia (St. Clair, D., (2008). *Schizophr Bull* 35(1):9-12).

Therefore, there is a need for methods of screening for copy number variations that employs an efficient, reproducible assay and detection system.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides methods for detecting genetic characteristics in a sample, including copy number variations (CNVs), insertions, deletions, translocations, polymorphisms and mutations. The invention employs the technique of interrogating loci from two or more target genomic regions using at least two fixed sequence oligonucleotides for each interrogated locus, and joining the fixed sequence oligonucleotides either directly or indirectly via ligation. The ligation products from different loci in a selected genomic regions comprise nucleic acid capture regions designed to include a region complementary to one or more capture probes on a solid support. The capture region comprises one or more detectable labels that identify a ligation product as originating from a specific target genomic region. Identification of ligation products from different target genomic regions is achieved by binding of the capture regions of the ligation products to complementary capture probes on the solid support.

In a specific embodiment, the invention provides an assay method for providing a statistical likelihood of a fetal aneuploidy comprising providing a maternal sample comprising maternal and fetal cell free DNA, interrogating one or more loci from a first target genomic region using sequence-specific oligonucleotides that comprise a capture region, interrogating one or more loci from a second target genomic region using sequence-specific oligonucleotides that comprise a capture region, detecting the isolated selected loci from the first and second target genomic regions via hybridization to an array, quantifying total counts of the isolated loci to determine a relative frequency of first and second target genomic regions, interrogating selected polymorphic loci from at least one target genomic region different from the first and second target genomic regions using sequence-specific oligonucleotides, detecting isolated selected polymorphic loci, quantifying total counts of the isolated selected polymorphic loci to calculate a percentage of the fetal cell free DNA in the maternal sample, calculating a statistical likelihood a fetal aneuploidy in the maternal sample, wherein the relative frequency of loci from the first target genomic region, the relative frequency of loci from the second target genomic region, and quantified counts from the isolated selected polymorphic loci to provide a statistical likelihood of the presence of a fetal aneuploidy.

In other specific embodiments, the invention provides an assay method determining the presence or absence of a fetal aneuploidy comprising providing a maternal sample comprising maternal and fetal cell free DNA, interrogating one or more loci from a first target genomic region using sequence-specific oligonucleotides that comprise a capture region, interrogating one or more loci from a second target genomic region using sequence-specific oligonucleotides that comprise a capture region, detecting the loci from the first and second target genomic regions via hybridization to an array, quantifying total counts of the loci to determine a relative frequency of first and second target genomic regions, and determining the presence or absence of a fetal aneuploidy in the maternal sample based on a deviation from expected counts of the isolated loci using the relative frequency of loci from the first target genomic region and the relative frequency of loci from the second target genomic region. In certain aspects, the deviation from expected counts is determined using a threshold level determined from a representative population of samples, and preferably a representative population comprising samples from patients of similar maternal age and/or gestational age.

In specific aspects, the interrogation of the loci from the first and second genomic regions uses hybridization followed by ligation. In more specific aspects, an amplification step is performed after the hybridization and ligation steps. In other specific aspects, the amplification is universal amplification using the polymerase chain reaction.

In preferred aspects, the ligation products from two or more different genomic regions are identified using a single solid support with capture probes; e.g., an array comprising capture probes complementary to multiple capture regions indicative of the different target genomic regions. Upon introducing a pool of ligation products originating from two or more different genomic regions to the array, ligation products having the same capture region will competitively hybridize to complementary capture probes on the array, and the relative frequency of ligation products from each genomic region can be estimated based on the amount of detected label bound to the capture probes. In this manner, the relative frequencies of the target genomic regions themselves may be determined. The relative frequencies of each target genomic region may be determined by identifying the binding of capture regions on the ligation products corresponding to each selected locus from each target genomic region to specific, known locations on the array, or by estimating total fluorescence from the array following binding of the ligation products originating from the target genomic regions.

In certain preferred embodiments, the capture regions and capture probes do not reflect the specific target genomic region nucleotide sequence, and are instead "engineered" sequences that serve as surrogates to identify specific target genomic regions; thus, the nucleotide sequence of the ligation product corresponding to the target genomic region does not need to be determined directly. The use of the capture regions on the ligation products allows the binding of the ligation products to the capture probes on the array to indicate the larger target genomic region from which the ligation product originates without the need to sequence the portion of the ligation product corresponding to the actual nucleotide sequence of the target genomic region. Because the capture regions and capture probes are engineered sequences, they can be thought of as "universal" sequences; that is, these capture regions and capture probes can be used in conjunction with any number of different assays, the only difference being the target sequence(s) associated with the capture region(s).

In one embodiment, the arrays of the present invention comprise capture probes that all have substantially the same sequence. In another embodiment, the arrays used comprise two to several different features with capture probes having substantially the same sequence. These arrays are in contrast to arrays known in the art that identify individual sequences by complementarity to individual features with each feature comprising a nucleic acid sequence different from the other features. The use of a single or a limited number of complementary capture probe sequences in the individual features on an array can simplify the biochemistry needed to create the array and reduce potential spurious differences in detection frequency resulting, e.g., from differences in binding affinity between the capture regions on the ligation products and the capture probes.

In specific embodiments, the arrays comprise two or more different capture probes used to detect individual ligation products from two or more different target genomic regions, two or more different loci from a single target genomic region, or two or more different alleles from a selected locus. That is, capture probes of different sequence hybridize to capture regions on ligation products that correspond to different target genomic regions, different loci from a single target genomic region, or different alleles from a selected locus. The capture regions on the ligation products are associated with labels indicative of the target genomic region or selected locus, or indicative of the alleles of a polymorphism, from which the ligation product originated.

Thus, it is a preferred embodiment of the invention that the ligation products are identified using a capture probe that is complementary to a capture region introduced in or to the ligation product, but that does not identify the target genomic region to which the ligation product corresponds solely by hybridization to a feature complementary to the target genomic region. In some embodiments, the capture probe is in part complementary to a target genomic region and in part complementary to a capture region in a ligation product. In a preferred embodiment, the capture region used to identify a ligation product which corresponds to a target genomic region is not complementary to any portion of the target genomic region.

Preferably the capture region is introduced as part of one of the fixed sequence oligonucleotides prior to ligation, although the capture region may be attached (e.g., via ligation of an adaptor) to one or both ends of the ligation product of the fixed sequence oligonucleotides following the ligation procedure.

It is another feature of the hybridization assay format of the invention that quantification of target genomic regions when using capture regions can be achieved by quantifying labels that are associated with the ligation products from the loci within the target genomic region without actually determining the sequence of the ligation products corresponding to the target genomic regions. In this manner, the frequency of ligation products from a target genomic region (and thus the frequency of the target genomic regions themselves) can be estimated without the need to detect the actual nucleotide sequence of the loci from that target genomic region.

In many preferred embodiments, quantification of the labels bound to the capture probes on the array is the only readout necessary to estimate the levels or amounts of ligation products produced from each target genomic region, which in turn can be used to estimate the frequency of the target genomic regions.

It is an advantage of the methods of the invention that the ligation products can be associated with multiple different detectable labels and/or capture regions. The use of different labels and/or capture regions in different experiments can mitigate any frequency bias from the use of a particular detectable label, capture region or capture probe.

In certain embodiments, the present invention provides methods for detecting frequencies of first and second target genomic regions in a sample comprising: introducing a first set of first and second fixed sequence oligonucleotides to a sample under conditions that allow the first and second fixed sequence oligonucleotides to hybridize specifically to complementary regions in loci from a first target genomic region, wherein at least one of the first or second fixed sequence oligonucleotide of the first set comprises a capture region and a first label; introducing a second set of first and second fixed sequence oligonucleotides to a sample under conditions that allow the first and second fixed sequence oligonucleotides to hybridize specifically to complementary regions in loci from a second target genomic region, wherein at least one of the first or second fixed sequence oligonucleotide of the second set comprises a capture region and a second label; ligating the hybridized fixed sequence oligonucleotides to create ligation products complementary to the loci; introducing the ligation products to an array comprising capture probes under conditions that allow the capture probes on the array to hybridize specifically to the capture regions of the ligation products; detecting the first and second labels; and quantifying a relative frequency of the first and second labels to quantify the relative frequency of the first and second target genomic regions. In some aspects, the capture regions of the first and second sets of ligation products are different. In other aspects the capture regions of the first and second sets of ligation products are the same.

In a preferred aspect, the first and second capture regions of the first and second sets of oligonucleotides are the same. In other aspects, a small number of capture regions are used in the fixed sequence oligonucleotides of both the first and the second set. In other aspects, the first capture regions corresponding to the first target genomic region are different from the second capture regions corresponding to the second genomic region.

In other preferred embodiments, in addition to interrogating first and second target genomic regions, polymorphic sequences comprising SNPs from two or more selected polymorphic loci also are interrogated. Selected polymorphic loci are interrogated using a third set of fixed sequence oligonucleotides to determine allele frequencies. The allele frequencies are used, e.g., to calculate the percent of fetal nucleic acids present in a maternal serum sample.

In certain embodiments, the first and second fixed sequence oligonucleotides do not hybridize adjacently to the loci in the target genomic regions, and instead have an intervening region or "gap" between the fixed sequence oligonucleotides of a set hybridized to a locus. This intervening region may be filled, e.g., using a polymerase and dNTPs to extend the end of one fixed sequence oligonucleotide so that the end becomes adjacent to the end of the other hybridized oligonucleotide of the set. In another embodiment, the intervening region may be filled using one or more "gap-filling" or "bridging" oligonucleotides that bind between and adjacent to the fixed sequence oligonucleotides of a set. In the latter case, preferably the ligation step will ligate all of the oligonucleotides into a single, contiguous ligation product comprising a single capture region which can then be detected on an array. In yet another embodiment, a combination of bridging oligonucleotides and dNTPs and polymerase can be used to fill the intervening space between the fixed sequence oligonucleotides.

In the above-described embodiments, a set of fixed sequence nucleic acids is used which comprises two separate fixed sequence oligonucleotides designed to hybridize to two separate regions in each selected locus (either adjacently or non-adjacently). In some embodiments, however, a set of fixed sequence oligonucleotides can comprise a single probe with regions at either end complementary to a selected locus. Upon hybridization of this single probe to a locus, the probe forms a circular structure that may or may not be adjacently hybridized on the locus. Such "precircle" probes can also hybridize with a gap between the ends of the probe, which gap may be filled by the hybridization of one or more bridging oligonucleotides, by extension of one end of the probe using polymerase and dNTPs, or a combination thereof.

In certain aspects, the detectable labels are directly associated with (i.e., covalently or non-covalently bound to a capture region that is in one of the fixed sequence oligonucleotides of each set. In another embodiment, the ligation products are amplified following ligation, e.g., in a universal amplification, and the detectable label is associated with a capture region contained within a primer used for the amplification. In other specific aspects, the isolated loci from the first and second target genomic regions and the ligation products from the selected polymorphic loci are amplified in a single vessel. In other aspects, the detectable labels are covalently or non-covalently bound to an oligonucleotide that hybridizes to a complementary sequence on the ligation products, amplicons or cleavage products thereof. Such labeled oligonucleotides may be hybridized to the ligation products prior to or after introduction of the ligation products to the capture probe array.

In other embodiments of the invention, the capture regions on the ligation products corresponding to different target genomic regions comprise different sequences, and the comparative frequency of at least a first and a second target genomic region are determined based on the use of different detectable labels associated with the different capture regions.

In certain aspects, copy number variants are is detected by an alteration of an expected ratio of bound detectable label from the bound ligation products from the target genomic regions in the sample. In certain specific aspects copy number variants are detected by an increased or decreased level of hybridization of a first set of ligation products from a first selected locus as compared to a second set of ligation products from a second selected locus.

The relative frequency of loci in a sample can be used to determine not only copy number variation for a small target genomic region, but also in conjunction with and/or in comparison to other loci, the relative frequency of loci may be used to determine the copy number variation of larger target genomic regions, including partial or whole chromosomes.

In another general aspect of the invention, a method for detecting frequencies of first and second target genomic regions in a sample is provided comprising introducing a first set of first and second fixed sequence oligonucleotides to a sample under conditions that allow the first and second fixed sequence oligonucleotides to hybridize specifically to complementary regions in loci in the first target genomic region to create first hybridized fixed sequence oligonucleotides; introducing a second set of first and second fixed sequence oligonucleotides to the sample under conditions that allow the first and second fixed sequence oligonucleotides to hybridize specifically to complementary regions to create second hybridized fixed sequence oligonucleotides; and ligating the hybridized fixed sequence oligonucleotides of each set to create ligation products complementary to loci in the first and second target genomic regions. At least one fixed sequence oligonucleotide of each set comprises a capture region comprising a sequence complementary to capture probes on an array and a binding region for a detectable label. The ligation products are introduced to the array comprising capture probes complementary to the capture regions of the ligation products under conditions that allow the capture probes to specifically hybridize to the capture regions of the ligation products. A first detectable label is introduced to the array under conditions that allow the detectable label to specifically hybridize to the binding region of the capture region on the ligation products from the loci from the first target genomic region, and a second detectable label is introduced to the array under conditions that allow the detectable label to specifically hybridize to the binding regions of the capture region on the ligation products from the loci from the second target genomic region. The first and second detectable labels are detected and quantified to provide a relative frequency of the first and second target genomic regions in the sample. As discussed, above, in relation to one embodiment, in addition to interrogating first and second target genomic regions, aspects of this embodiment interrogate polymorphic sequences comprising SNPs from two or more selected polymorphic loci. Selected polymorphic loci are interrogated using a third set of fixed sequence oligonucleotides to determine allele frequencies. The allele frequencies are used, e.g., to calculate the percent of fetal nucleic acids present in a maternal serum sample. Also as discussed, above, in some aspects of this embodiment, "gap-filling" or "bridging" oligonucleotides may be employed in addition to the two fixed sequence oligonucleotides, and in some aspects of this embodiment, the fixed sequence oligonucleotides or the bridging oligonucleotides are allele-specific, as described in detail infra.

In specific aspects, the assay of the invention provides identifying low frequency alleles from the isolated selected polymorphic loci where the maternal DNA is homozygous and the non-maternal DNA is heterozygous, computing a sum of low frequency alleles from the isolated selected polymorphic loci, and calculating a statistical likelihood of a fetal aneuploidy in the maternal sample using the sum of the low frequency alleles from the isolated selected polymorphic loci to calculate statistically significant differences in target genomic region frequencies for the first and second target genomic regions, and wherein a statistically significant difference in chromosomal frequency provides a statistical likelihood of the presence of a fetal aneuploidy.

In yet another general aspect of the invention, a method is provided for detecting frequencies of first and second target genomic regions in a sample, the method comprising providing a sample; introducing a first set of first and second fixed sequence oligonucleotides to the sample under conditions that allow the fixed sequence oligonucleotides to hybridize specifically to complementary regions in first loci of the first target genomic region to create first hybridized fixed sequence oligonucleotides; and introducing a second set of first and second fixed sequence oligonucleotides to the sample under conditions that allow the fixed sequence oligonucleotides to hybridize specifically to complementary regions in second loci of the second target genomic region to create second hybridized fixed sequence oligonucleotides. At least one of the fixed sequence oligonucleotides of the first set of fixed sequence oligonucleotides comprises a capture region and a label binding region complementary to a first detectable label, and at least one of the fixed sequence oligonucleotides of the second set of fixed sequence oligonucleotides comprises substantially the same capture region as the first set and a label binding region complementary to a second detectable label. The fixed sequence oligonucleotides of the first and second set are ligated to create first and second ligation products comprising regions complementary to the first and second loci, respectively, and labeled with a first and second detectable label. The first and second ligation products are introduced to an array comprising capture probes under conditions that allow the capture probes to specifically hybridize to the capture regions of the ligation products. The first and second labels are detected and quantified to determine a relative frequency of the first and second labels, thereby quantifying a relative frequency of the first and second target genomic regions in the sample.

The detectable labels may be introduced to the ligation products prior to the introduction of the ligation products to the array. Alternatively, the detectable labels may be introduced to the array following hybridization of the ligation products.

Again, in certain embodiments, the methods further employ the extension of at least one fixed sequence oligonucleotide hybridized to a sequence of interest. That is, in some embodiments the fixed sequence oligonucleotides that hybridize to one or more loci may not hybridize adjacently, leaving a "gap" or "intervening" region. This intervening region may be filled, e.g., using a polymerase and dNTPs to extend the end of one fixed sequence oligonucleotide so that the end is adjacent to the end of the other hybridized fixed sequence oligonucleotide of the set. In another embodiment, the intervening region may be filled using one or more "gap-filling" or "bridging" oligonucleotides that bind between and adjacent to the fixed sequence oligonucleotides of a set. In the latter case, preferably the ligation step will ligate all of the oligonucleotides into a single, contiguous ligation product comprising a single capture region which can then be detected on an array. Also, a combination of bridging or gap-filling oligonucleotides and dNTPs and polymerase can be used to fill the gap. Additionally in some embodiments, pre-circular, padlock or molecular inversion probes may be used in lieu of two fixed sequence oligonucleotides in a set.

When gap-filling or bridging oligonucleotides are used, the bridging oligonucleotides typically are short, preferably between 2-30 nucleotides and more preferably between 3-28 nucleotides in length. In one aspect, the bridging oligonucleotides can be designed to provide degeneracy at multiple or all positions, e.g., the bridging oligonucleotides may be full or partial randomers with various sequence variations to ensure detection of the loci even if a locus contains a polymorphic nucleotide at one or more positions. The degeneracy of the bridging oligonucleotide can be designed based on the predicted polymorphisms that may be present in the loci. Alternatively, in another aspect the pool of bridging oligonucleotides used in a reaction can provide limited degeneracy targeting specifically one or more positions based on predicted polymorphisms that may be present in the regions of the loci. In yet another aspect, the pool of bridging oligonucleotides used in a reaction can provide degeneracy for each internal position, with the nucleotides adjacent to the sites of ligation with the fixed sequence oligonucleotides remaining fixed. It is an advantage that using degenerate bridging oligonucleotides obviates the need to predetermine the maternal and fetal polymorphic content for a selected locus prior to employing the detection methods of the present invention.

In another aspect, the bridging oligonucleotide is longer than 10 nucleotides in length and is preferably 18-30 nucleotides in length. In a preferred aspect, there is a single bridging oligonucleotide complementary to each selected locus designed to hybridize between the regions of the selected locus complementary to the first and second fixed sequence oligonucleotides. In another aspect, two or more bridging oligonucleotides are designed to hybridize between the fixed sequence oligonucleotides at each selected locus, and preferably the bridging oligonucleotides hybridize adjacently to the first and second fixed sequence oligonucleotides.

In the situation where there are two bridging oligonucleotides, three ligation events occur per selected locus: ligation between the first fixed oligonucleotide and the first bridging oligonucleotide, ligation between the first and second bridging oligonucleotides, and ligation between the second bridging oligonucleotide and the second fixed sequence oligonucleotide. In another aspect, there may be gaps between the bridging oligonucleotides and/or between the bridging oligonucleotides and the fixed sequence oligonucleotides. These gaps can be filled by extension—e.g., by use of polymerase and dNTPs—prior to ligation.

In one aspect of the invention, the first and second fixed sequence oligonucleotides are introduced to the sample and specifically hybridized to the complementary portions of the loci prior to introducing the bridging oligonucleotides to the sample. In another aspect, the bridging oligonucleotides are introduced to the sample at the same time the first and second sets of fixed sequence oligonucleotides are introduced to the sample.

In another general aspect of the invention, a method for determining a presence or absence of an aneuploidy in a mixed sample is provided, the method comprising providing a mixed sample; introducing a first set of first and second fixed sequence oligonucleotides to the mixed sample under conditions that allow the fixed sequence oligonucleotides to hybridize specifically to first loci on a first chromosome to create first hybridized fixed sequence oligonucleotides, where the first set of fixed sequence oligonucleotides comprises a first capture region and a first label binding region; introducing a second set of first and second fixed sequence oligonucleotides to the mixed sample under conditions that allow the fixed sequence oligonucleotides to hybridize specifically to second loci on a second chromosome to create second hybridized fixed sequence oligonucleotides, where the second set of fixed sequence oligonucleotides comprises a second capture region and a second label binding region; ligating the hybridized oligonucleotides to create ligation products complementary to the loci; introducing the ligation products to an array comprising capture probes under conditions that allow the capture probes to hybridize specifically to the first and second capture regions of the ligation products; introducing a first labeled oligonucleotide to the array under conditions that allow a target recognition region of the first labeled oligonucleotide to hybridize specifically to the first label binding region; introducing a second labeled oligonucleotide to the array under conditions that allow a target recognition region of the second labeled oligonucleotide to hybridize specifically to the second label binding region; detecting first and second labels; quantifying relative frequencies of the first and second labels, thereby quantifying a relative frequency of the first and second chromosome (or genomic region) in the mixed sample, wherein a statistically significant difference in the relative frequencies of the labels on the array is indicative of the presence or absence of a chromosomal aneuploidy in the mixed sample.

In alternative embodiments, a "threshold" level can be used to determine the presence or absence of a fetal aneuploidy based on the observed deviation of the relative frequency of the first and second chromosome in the mixed sample. This threshold may be determined, e.g., using techniques such as those disclosed in U.S. App. 2012/0149583, 2013/0324420, 2013/0029852 and U.S. Pat. No. 8,532,936. In certain aspects, the deviation from expected counts is determined using a threshold level determined from a representative population of samples, and preferably a representative population comprising samples from patients of similar characteristics, such as prior risk profile, maternal age and/or gestational age.

In preferred aspects of the invention, the sample DNA is bound to a solid support, either before, during or after the addition of the fixed sequence oligonucleotides. In preferred aspects of the invention, the assays employ steps to remove unhybridized oligonucleotides prior to creation of ligation products, e.g., by washing or by exonuclease digestion. In other preferred aspects, the ligation products are isolated following ligation but prior to further processing and/or introduction to the array for detection. In other preferred embodiments, the ligation products are amplified, preferably using universal primers, to form amplicons. In other preferred embodiments, the amplicons are subsequently cleaved to form cleaved amplicons before hybridization to an array. In embodiments involving cleavage of the ligation products, the cleaved region comprising the capture regions is preferably separated from the remainder of the cleavage products prior to introduction of the capture region portion to the array.

In certain aspects, the sample DNA, ligations products and/or the amplification products are isolated using conventional techniques in the art. For example, the hybridization complexes (e.g., the fixed sequence oligonucleotides bound to the target loci), ligations products and/or the amplification products may be isolated by attachment to a solid substrate followed by a separation step, e.g. washing or nuclease digestion. In specific examples, they may be isolated using attachment to magnetic beads. In other specific examples, they may be isolated using attachment to a substrate with a binding partner, e.g. the oligonucleotide is biotinylated and the substrate comprises avidin or streptavidin. In aspects in which precircle probes are used, the hybridization complexes and/or ligation products may be isolated by nuclease destruction of non-circularlized probes.

In some aspects of this embodiment, the first and second capture regions have the same nucleotide sequence. In other aspects of this embodiment, the first and second capture regions have different nucleotide sequences. Also as discussed, above, in relation to other embodiments, in addition to interrogating first and second target genomic regions, aspects of this embodiment interrogate polymorphic sequences comprising SNPs from two or more selected polymorphic loci. Selected polymorphic loci are interrogated, e.g., using a third set of fixed sequence oligonucleotides to determine allele frequencies. The allele frequencies are used, e.g., to calculate the percent of fetal nucleic acids present in a maternal serum sample.

As discussed above, in some aspects of this embodiment, extension ligation and/or "bridging" oligonucleotides may be employed in addition to the two fixed sequence oligonucleotides. Accordingly, the invention provides a method for determining a likelihood of a fetal aneuploidy comprising the steps of providing a maternal sample comprising maternal and fetal cell free DNA, introducing first sets of two fixed sequence oligonucleotides complementary to loci in a first target genomic region in the maternal sample under conditions that allow a complementary region of each fixed sequence oligonucleotide to specifically hybridize to the loci, wherein at least one of the two fixed sequence oligonucleotides of each set comprises a universal primer site and a capture region, introducing second sets of two fixed sequence oligonucleotides complementary to loci in a second target genomic region in the maternal sample under conditions that allow a complementary region of each fixed sequence oligonucleotide to specifically hybridize to the loci, wherein at least one of the two fixed sequence oligonucleotides of each set comprises a universal primer site and a capture region, introducing third sets of two fixed sequence oligonucleotides complementary to a set of polymorphic loci in a target genomic region that is different from the first target genomic region in the maternal sample under conditions that allow a complementary region of each fixed sequence oligonucleotide to specifically hybridize to selected polymorphic loci, wherein at least one of the two fixed sequence oligonucleotides of each set comprises a universal primer site and a capture region, introducing bridging oligonucleotides to the maternal sample under conditions that allow the bridging oligonucleotides to specifically hybridize to complementary regions in the loci between the fixed sequence oligonucleotides, ligating the hybridized first and second fixed sequence oligonucleotides and the bridging oligonucleotides to create ligation products complementary to the loci, isolating the ligation products, amplifying the isolated ligation products using the universal primer sites, applying the amplified ligation products to an array, wherein the array comprises capture probes complementary to the capture regions on the ligation products, quantifying a relative frequency of each allele from the selected polymorphic loci to determine a percent fetal cell-free DNA in the sample, quantifying a relative frequency of loci from the first target genomic region and a relative frequency of loci from the second target genomic region, and computing a likelihood of the presence or absence of a fetal aneuploidy using the relative frequency of the loci from the first and second target genomic regions and the percent fetal cell-free DNA to determine the likelihood of the presence or absence of a fetal aneuploidy.

The invention also provides a method for determining a likelihood of a fetal aneuploidy comprising the steps of providing a maternal sample comprising maternal and fetal cell free DNA, introducing first sets of two fixed sequence oligonucleotides complementary to loci in a first target genomic region in the maternal sample under conditions that allow a complementary region of each fixed sequence oligonucleotide to specifically hybridize to the loci, wherein at least one of the two fixed sequence oligonucleotides of each set comprises a universal primer site and a capture region, introducing second sets of two fixed sequence oligonucleotides complementary to loci in a second target genomic region in the maternal sample under conditions that allow a complementary region of each fixed sequence oligonucleotide to specifically hybridize to the loci, wherein at least one of the two fixed sequence oligonucleotides of each set comprises a universal primer site and a capture region, introducing third sets of two fixed sequence oligonucleotides complementary to a set of polymorphic loci in a target genomic region that is different from the first target genomic region in the maternal sample under conditions that allow a complementary region of each fixed sequence oligonucleotide to specifically hybridize to selected polymorphic loci, wherein at least one of the two fixed sequence oligonucleotides of each set comprises a universal primer site and a capture region, extending at least one of the hybridized fixed sequence oligonucleotides using dNTPs and a polymerase to create adjacently hybridized oligonucleotides, ligating the adjacently hybridized oligonucleotides to create ligation products complementary to the loci, isolating the ligation products, amplifying the isolated ligation products using the universal primer sites, applying the amplified ligation products to an array, wherein the array comprises capture probes complementary to the capture regions on the ligation products, quantifying a relative frequency of each allele from the selected polymorphic loci to determine a percent fetal cell-free DNA in the sample, quantifying a relative frequency of loci from the first target genomic region and a relative frequency of loci from the second target genomic region, and computing a likelihood of the presence or absence of a fetal aneuploidy using the relative frequency of the loci from the first and second target genomic regions and the percent fetal cell-free DNA to determine the likelihood of the presence or absence of a fetal aneuploidy.

In certain aspects, the invention further comprises comparing the relative frequency of the loci from the first and second target genomic regions and adjusting the relative frequency of the loci from the first and second target genomic regions based on the percent fetal cell-free DNA to determine the likelihood of the presence or absence of a fetal aneuploidy. In specific aspects, the relative frequencies of each selected locus for each target genomic region are summed and the sums for each chromosome are compared to calculate a target genomic region ratio.

The percent fetal cell free DNA of a sample can be calculated by detecting levels of one or more non-maternal contributed loci, e.g., non-maternal loci on the Y-chromosome and/or non-maternal loci are autosomal loci. In preferred aspects, the non-maternal loci comprise one or more genetic variations compared to maternal loci, e.g., SNPs or methylation differences.

In certain embodiments, the ligation products are cleaved (e.g., using enzymatic cleaving mechanisms such as a restriction endonuclease) to reduce the size of the ligation product while leaving the capture region and label binding region available for detection. In certain aspects, the cleavage occurs after the universal amplification.

In preferred embodiments, the loci and fixed sequence oligonucleotides hybridized to the loci are isolated from unbound fixed sequence oligonucleotides following hybridization to remove excess unbound oligonucleotides in the reaction; e.g., through a washing step or enzymatic degradation of the unbound oligonucleotides.

The first and second sets of fixed sequence oligonucleotides used in the methods preferably comprise—in addition to at least one capture region—universal primer regions that may be used to amplify the ligation products. Alternatively, universal primer sequences may be added to the ends of the ligation products following ligation, e.g., through the introduction of adapters comprising universal primer sequences.

In certain aspects, the fixed sequence oligonucleotides of the invention comprise one or more indices. These indices may serve, in addition to the capture regions, as surrogate sequences to identify the loci, or a particular allele of a locus. In particular, these indices may serve as surrogate identification sequences to detect hybridization of the ligation product or amplicons thereof to an array. In specific methods, the first or second fixed sequence oligonucleotide in each set of fixed sequence oligonucleotides comprises an allele index that associates a specific allele with the fixed sequence oligonucleotide.

In certain specific aspects, the method is carried out for at least 50 loci from each target genomic region, more preferably between 50-100 loci, more preferably between 100-200 loci, more preferably between 200-500 loci, more preferably between 500-1000 loci, preferably between 1000-2000 loci, preferably between 2000-5000 loci, and preferably between 5000-10,000 loci from a target genomic region, or any intervening range therein. In certain aspects, in addition to the target genomic regions, at least 50 selected polymorphic loci are interrogated. More preferably, between 50-100 selected polymorphic loci are interrogated, more preferably between 100-200 selected polymorphic loci, more between 200-500 selected polymorphic loci, more between 500-1000 selected polymorphic loci, between 1000-2000 selected polymorphic loci, between 2000-5000 selected polymorphic loci, and between 5000-10,000 selected polymorphic loci are interrogated, including all intervening ranges.

In other aspects, the assay methods are estimated to detect at least 5 capture regions corresponding to each locus within a target genomic region, more preferably at least 10 capture regions corresponding to each locus within a target genomic region, more preferably at least 20 capture regions corresponding to each locus within a target genomic region, preferably at least 50 capture regions corresponding to each locus within a target genomic region, more preferably at least 100 capture regions corresponding to each locus within a target genomic region, more preferably at least 200 capture regions corresponding to each locus within a target genomic region. In some embodiments, no more than 5000 capture regions corresponding to each locus within a target genomic region are detected for each sample. In other embodiments no more than 2000 capture regions corresponding to each locus within a target genomic region are detected for each sample.

These aspects and other features and advantages of the invention are described in more detail below.

DEFINITIONS

Figure 1:
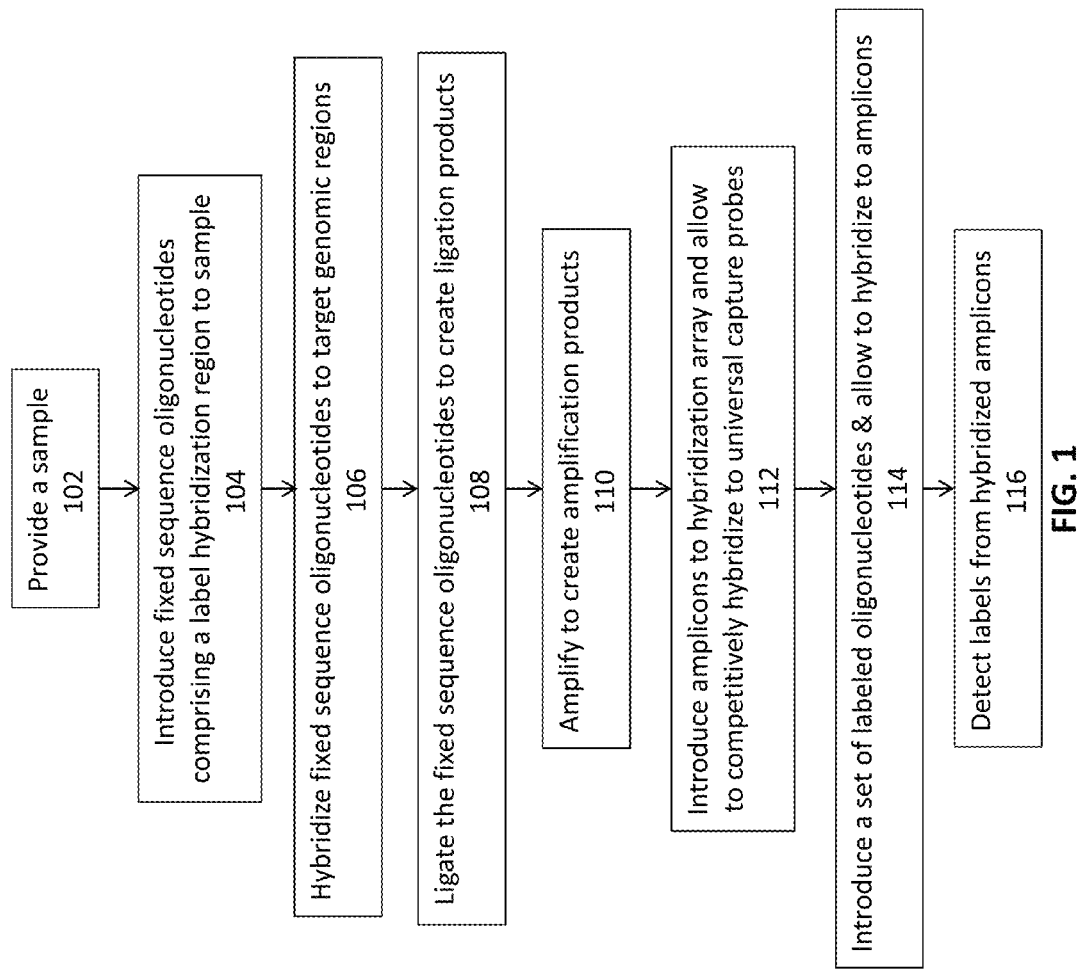
FIG. 1 is a flow chart describing one general aspect of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "allele index" refers generally to a series of nucleotides that corresponds to a specific SNP. The allele index may contain additional nucleotides that allow for the detection of deletion, substitution, or insertion of one or more bases. The allele index may be combined with any other index to create one index that provides information for two properties (e.g., sample-identification index, allele-locus index).

"Array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using an array. The term array refers to any format of arrayed solid substrates, including a microarray, arrayed beads, an array of molecules within wells, or "liquid" arrays.

The term "binding pair" means any two molecules that specifically bind to one another using covalent and/or non-covalent binding, and which can be used, e.g., for attachment of genetic material to a substrate. Examples include, but are not limited to, ligands and their protein binding partners, e.g., biotin and avidin, biotin and streptavidin, an antibody and its particular epitope, and the like.

The term "chromosomal abnormality" refers to any genetic variant for all or part of a chromosome. The genetic variants may include but are not limited to any copy number variant such as duplications or deletions, translocations, inversions, and mutations.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "diagnostic tool" as used herein refers to any composition or system of the invention used in combination as, for example, in a system in order to carry out a diagnostic test or detection system on a patient sample.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

As used herein the term "ligase" refers generally to a class of enzymes, DNA ligases (typically T4 DNA ligase), which can link pieces of DNA together. The pieces must have compatible ends—either with both of them blunt or with mutually-compatible sticky ends—and the reaction requires ATP. "Ligation" is the process of joining two pieces of DNA together.

The terms "locus" and "loci" as used herein refer to a nucleic acid region of known location in a genome.

The term "maternal sample" as used herein refers to any sample taken from a pregnant mammal which comprises both fetal and maternal cell-free DNA. Preferably, maternal samples for use in the invention are obtained through relatively non-invasive means, e.g., phlebotomy or other standard techniques for extracting peripheral samples from a subject.

The term "oligonucleotides" or "oligos" as used herein refers to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both of which are incorporated herein by reference, or by other chemical methods such as using a commercial automated oligonucleotide synthesizer.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes or variants in a loci that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques. A primer may also be used in hybridization techniques as a means to provide complementarity of a nucleic acid region to a capture oligonucleotide for detection of a specific nucleic acid region.

The term "research tool" as used herein refers to any composition or system of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample" refers to any sample comprising all or a portion of the genetic information of an organism, including but not limited to virus, bacteria, fungus, plants and animals, and in particular mammals. The genetic information that can be interrogated within a genetic sample includes genomic DNA (both coding and non-coding regions), mitochondrial DNA, RNA, and nucleic acid products derived from each of these. Such nucleic acid products include cDNA created from mRNA or products of pre-amplification to increase the material for analysis.

The term "target genomic region" refers to all or a portion of a chromosome or chromosomes, including complete chromosomes, sub-chromosomal regions, groups of loci and single loci.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and array technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* (4th Ed.) W.H. Freeman, New York N.Y.; Gait, "*Oligonucleotide Synthesis: A Practical Approach*"1984, IRL Press, London; Nelson and Cox (2000), *Lehninger, Principles of Biochemistry* $3^{rd}$ Ed., W. H. Freeman Pub., New York, N.Y.; and Berg et al. (2002) *Biochemistry*, $5^{th}$ Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "an allele" refers to one or more copies of allele with various sequence variations, and reference to "the detection system" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference in their entirety for all purposes, including the purpose of describing and disclosing devices, reagents, techniques and methodologies that may be used in or in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The invention provides assay methods to identify copy number variants of nucleic acid regions (including loci, sets of loci and larger target genomic regions, e.g., chromosomes), including insertions, deletions, translocations, mutations and polymorphisms in a genetic sample. In one aspect, the assay methods interrogate loci from two or more target genomic regions in a sample using a directed ligation assay followed by detection of labelled oligonucleotides attached to an array. Quantification of the labelled oligonucleotides allows determination of an atypical copy number of a particular target genomic region based on a comparison between the quantities of detected loci from the target genomic regions (e.g., comparison between two or more portions of a single chromosome or comparison between two or more different chromosomes) in the sample or by comparison to a reference chromosome from the same or a different sample.

In some embodiments, the method employs directed analysis of target genomic regions in a sample using sets of fixed sequence oligonucleotides that selectively hybridize to loci within two or more target genomic regions. The fixed sequence oligonucleotides are directly or indirectly ligated to create ligation products. The ligation products corresponding to loci associated with a first target genomic region are associated with a first detectable label and ligation products corresponding to loci associated with a second target genomic region are associated with a second detectable label. If the first and second detectable labels are quantified, the relative frequency of each of the first and second target genomic regions can be determined. In certain aspects of the invention, the method employs two different labels that are used to identify two different target genomic regions. In other aspects of the invention, the method employs three different labels corresponding to three different target genomic regions, and so on.

The ligation products are detected by hybridization, and in particular by hybridization to an array of capture probes complementary to capture regions present in the ligation products. In certain embodiments, the ligation products are detected using "universal arrays" that comprise features having the same or substantially similar capture probes. In certain other embodiments, the arrays comprises two or more sets of multiple features with a common sequence, with each set having a different sequence, e.g., an array where up to hundreds of the features on the array have substantially the same sequence. In either case, the capture probes on the array are complementary to the capture regions of the ligation products rather than to the sequence of the loci or their complements. These arrays can be used to interrogate any loci for any target genomic region(s) regardless of the sequence of the loci.

The capture regions are preferably introduced to the ligation products in the fixed sequence oligonucleotides that are used to interrogate the loci in the sample. In some preferred embodiments, the capture regions are the same amongst all fixed sequence oligonucleotides used, so that ligation products or amplicons or cleavage products thereof from all loci hybridize competitively to capture probes of the same sequence on the array. In other embodiments, the array is comprised of many different capture probes, and the sets of fixed sequence oligonucleotides from different loci comprise different capture regions.

FIG. 1 is a flow chart 100 illustrating an exemplary method of the invention. In step 102, a sample is provided. In step 104, sets of fixed sequence oligonucleotides comprising a label binding region are introduced to the sample under conditions that allow the fixed sequence oligonucleotides to hybridize to loci in target genomic regions, and in step 106 the oligonucleotides are hybridized to the target genomic regions. In step 108, the hybridized fixed sequence oligonucleotides from each set are ligated to create ligation products which are then amplified in step 110 to produce amplicons complementary to the ligation products. In step 112, the amplicons are introduced to a hybridization array and allowed to hybridize competitively to capture probes on the array. In step 114, a set of labelled oligonucleotides are introduced to the amplicons and allowed to hybridize to complementary sequences on the amplicons. Optionally, the labelled oligonucleotides are ligated to the capture probe on the array (not shown). In step 116, the labels are detected.

Figure 2:
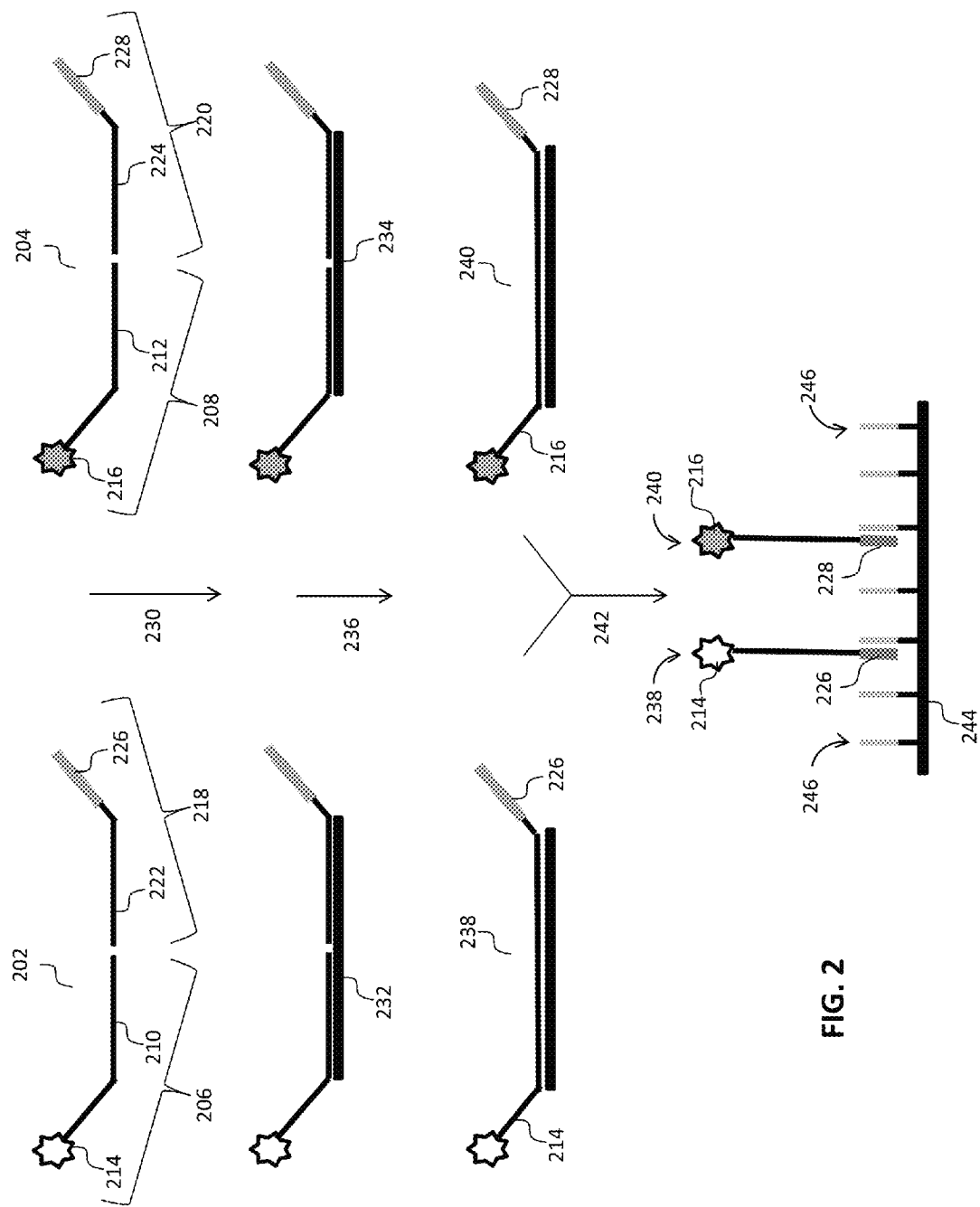
FIG. 2 illustrates an embodiment of a method of the invention that utilizes hybridization detection of loci.

Each fixed sequence oligonucleotide of each set comprises a region complementary to a selected locus (as described in more detail in FIG. 2). At least one fixed sequence oligonucleotide of each set further comprises a capture region, which may be the same for all sets of fixed sequence oligonucleotides used to interrogate two or more target genomic regions, may be the same for pairs of sets of fixed sequence oligonucleotides used to interrogate two or more target genomic regions, or may be different between sets of fixed sequence oligonucleotides for individual target genomic regions. Additionally, depending on the embodiment, one fixed sequence oligonucleotide of a set comprises either a detectable label or a label binding region for association of the fixed sequence oligonucleotide with the detectable label. In specific embodiments, the label binding region can be a region complementary to a labeled oligonucleotide associated with a detectable label.

Figure 3:
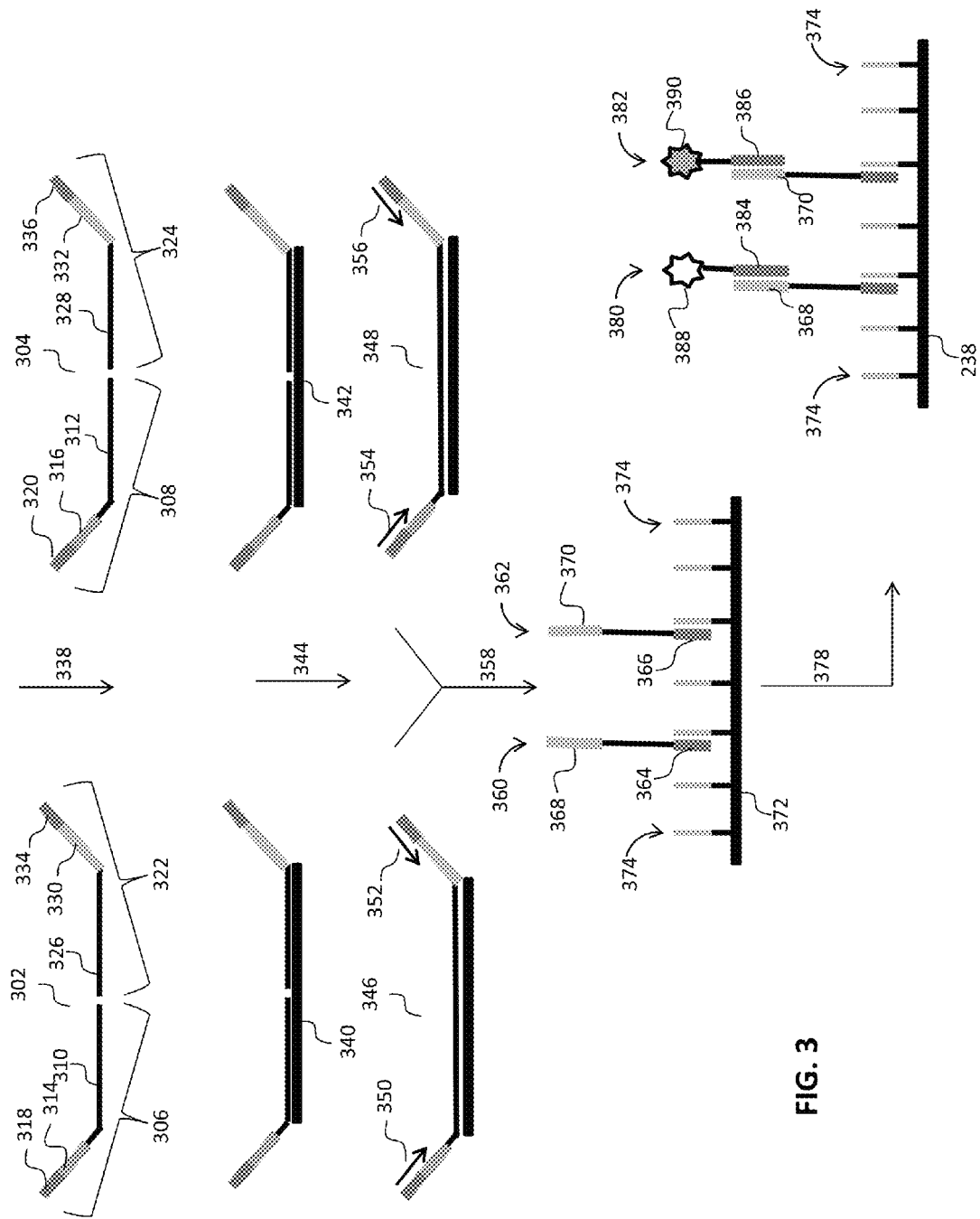
FIG. 3 illustrates an alternative embodiment of a method of the invention that utilizes hybridization detection of loci.
Figure 4:
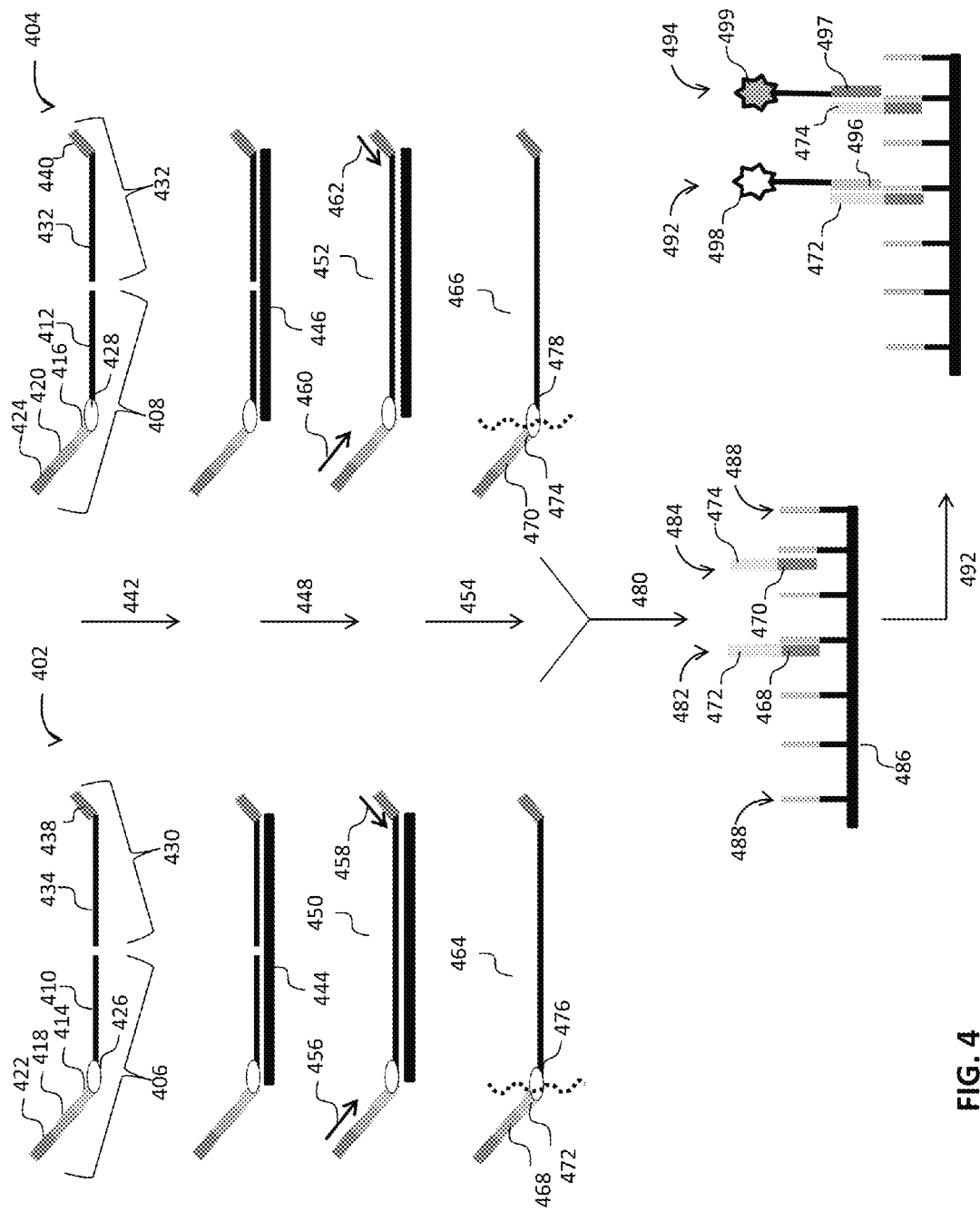
FIG. 4 illustrates another alternative embodiment of a method of the invention that utilizes hybridization detection of loci.

In some embodiments, the fixed sequence oligonucleotide of each set that comprises the capture region will not comprise the label or label binding region; that is, the other fixed sequence oligonucleotide of the set comprises the label or label binding region (see, e.g., exemplary embodiments illustrated in FIGS. 2, 3 and 5-8); in other embodiments, the fixed sequence oligonucleotide of each set that comprises the capture region also will comprise the label or label binding region (see, e.g., exemplary embodiment illustrated in FIG. 4).

In certain specific aspects, a first set of fixed sequence oligonucleotides hybridizes to loci in a first target genomic region while a second set of fixed sequence oligonucleotides hybridizes to loci in a second target genomic region. After ligation to produce ligation products, the ligation products are optionally amplified using universal primers, and then are hybridized to an array. In other embodiments, the amplification product is cleaved (e.g., using a restriction endonuclease) and a portion of the amplification product comprising the capture region is introduced to the array for hybridization and detection. In preferred embodiments, each set of fixed sequence oligonucleotides used to interrogate a target genomic region contains the same label or label binding region. That is, all of the fixed sequence oligonucleotides of the first set are associated with a first label, all of the fixed sequence oligonucleotides of the second set are associated with a second label, and all of the fixed sequence oligonucleotides in a third set are associated with a third label.

If the fixed sequence oligonucleotides are labeled directly, the ligation products, amplicons or cleavage products thereof can be hybridized to the capture probes on the array and detected by readout from the labels. If the fixed sequence oligonucleotides instead contain a label binding region that is complementary to a labeled oligonucleotide (a "label binding sequence"), a labeled oligonucleotide must be added to the ligation product or amplicons before detection. In either scenario, the labels are then detected and quantified and the relative frequency of each label determined. Quantifying each label allows for quantification of each target genomic region.

In some embodiments, all sets of first and second fixed sequence oligonucleotides contain substantially the same capture region. In these embodiments, because ligation products from all loci from all target genomic regions share the same capture region complementary to the capture probes on the array, the ligation products from each target genomic region compete to hybridize to the capture probes on a universal array.

In other embodiments, the capture probes on an array comprise multiple sequences complementary to different capture regions, and the array comprises features that contain these different capture probes. In some such embodiments, each capture probe may hybridize to an unique capture region. In other such embodiments, more than one capture probe, representing loci from different genomic regions, may hybridize to a single capture region.

In other embodiments, different loci from the same or different target genomic regions may be configured to competitively hybridize against one another and thus would comprise the same capture region, while other loci from the same or different target genomic regions may be configured to competitively hybridize against one another, depending on the assay.

The target genomic regions may be large genomic regions, such as whole chromosomes, or may be smaller genomic regions such as sub-regions of a single chromosome or sub-regions on different chromosomes, even down to a single locus. Thus, the invention may be used to detect genomic variations such as aneuploidies and partial aneuploidies, as well as mutations, SNPs, rearrangements, insertions and deletions. In the case where whole chromosomes are compared, the first target genomic region may be, e.g., chromosome 21, and all loci to be interrogated with the first set of fixed sequence oligonucleotides will be from chromosome 21.

In the ligation assay, if the fixed sequence oligonucleotides bind to immediately adjacent regions in a selected locus, the fixed oligonucleotides may be ligated to create ligation products which are associated with target genomic region-specific labels. In the case where fixed sequence oligonucleotides do not bind to immediately adjacent regions within the genomic region—i.e., there is a gap between the hybridized fixed sequence oligonucleotides—the gap can be closed using primer extension, and/or one or more bridging oligonucleotides. Once the oligonucleotides are hybridized contiguously, either directly or following an extension operation or introduction of a bridging oligonucleotide, they may then be ligated to create ligation products which are associated with target genomic region-specific labels.

In certain aspects, a first set of fixed sequence oligonucleotides are selective for a first chromosome or first target genomic region and a second set of fixed sequence oligonucleotides are selective for a different chromosome or second target genomic region. FIG. 2 illustrates one embodiment in which each set of labeled fixed sequence oligonucleotides hybridize to loci on different chromosomes and ligation products are evaluated competitively on an array comprising capture probes. Two sets of labeled fixed sequence oligonucleotides 202, 204 are provided, each set having a first fixed sequence oligonucleotide 206, 208 comprising a sequence that is complementary to a selected locus 210, 212 and a label 214, 216 and a second fixed sequence oligonucleotide 218, 220 comprising a sequence complementary to the selected locus 222, 224 and a capture region 226, 228. The labels 214, 216 are different for each set of fixed sequence oligonucleotides to allow differentiation between the first target genomic region (in this case, a first chromosome) and the second target genomic region (in this case, a second chromosome) during detection. In step 230, the sets of fixed sequence oligonucleotides 202, 204 are introduced to a sample and allowed to hybridize to loci 232, 234 on two different chromosomes. Following hybridization, the unhybridized fixed sequence oligonucleotides preferably are separated from the remainder of the sample (not shown). In step 236, the fixed sequence oligonucleotides are ligated to create ligation products 238, 240 comprising capture regions 226, 228 and labels 214, 216. Although the fixed sequence oligonucleotides are illustrated in FIG. 2 as being hybridized adjacently in the loci, there may also be a gap that can be filled, e.g. using an extension reaction or using a bridging oligonucleotide that hybridizes adjacently between the fixed sequence oligonucleotides. In step 242, the ligation products 238, 240 are introduced to a hybridization array 244 comprising a plurality of capture probes 246 wherein the capture regions 226, 228 of the ligation products 238, 240 competitively hybridize to the capture probes 246. In a preferred embodiment, 226 and 228 have substantially the same sequence. Following hybridization of the ligation products to the array, unhybridized ligation products preferably are removed from the array (not shown). The labels 214, 216 can then be detected using an appropriate detection mechanism depending on the type of label used and the loci corresponding to each of the first and second chromosomes can be quantified to determine the presence and amount of each chromosome in the genetic sample.

According to the present invention, a "nucleotide" may be unlabeled or detectably labeled by well-known techniques. Fluorescent labels and their attachment to oligonucleotides are described in many reviews, including Haugland, *Handbook of Fluorescent Probes and Research Chemicals*, 9th Ed., Molecular Probes, Inc., Eugene Oreg. (2002); Keller and Manak, *DNA Probes*, 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo)benzoic acid (DABCYL), CASCADE BLUE® (pyrenyloxytrisulfonic acid), OREGON GREEN™ (2',7'-difluorofluorescein), TEXAS RED™ (sulforhodamine 101 acid chloride), Cyanine and 5-(2'-aminoethyl)aminonaphthalene-1-sulfonic acid (EDANS). Specific examples of fluroescently labeled nucleotides include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, CASCADE BLUE®-7-UTP (pyrenyloxytrisulfonic acid-7-UTP), CASCADE BLUE®-7-dUTP (pyrenyloxytrisulfonic acid-7-dUTP), fluorescein-12-UTP, fluorescein-12-dUTP, OREGON GREEN™ 488-5-dUTP (2',7'-difluorofluorescein-5-dUTP), RHODAMINE GREEN™-5-UTP ((5-{2-[4-(aminomethyl)phenyl]-5-(pyridin-4-yl)-1H-i-5-UTP)), RHODAMINE GREEN™-5-dUTP ((5-{2-[4-(aminomethyl)phenyl]-5-(pyridin-4-yl)-1H-i-5-dUTP)), tetramethylrhodamine-6-UTP, tetramethylrhodamine-6-dUTP, TEXAS RED™-5-UTP (sulforhodamine 101 acid chloride-5-UTP), TEXAS RED™-5-dUTP (sulforhodamine 101 acid chloride-5-dUTP), and TEXAS RED™-12-dUTP (sulforhodamine 101 acid chloride-12-dUTP) available from Molecular Probes, Eugene, Oreg.

In certain aspects of the invention, nucleic acids from the sample are associated with a substrate—e.g., using binding pairs such as, e.g., biotin and streptavidin, to attach the genetic material to a substrate surface or direct covalent attachment—before adding the sets of fixed sequence oligonucleotides to the sample. Briefly, a first member of a binding pair (e.g., biotin) can be associated with nucleic acids from the sample, and the nucleic acids attached to a substrate via a second member of the binding pair (e.g., avidin or streptavidin) on the surface of the substrate. Attachment of the nucleic acids from the sample can be particularly useful in removing unhybridized oligonucleotides following hybridization of the fixed sequence oligonucleotides and/or the bridging oligonucleotides to the loci. Briefly, the nucleic acids from the sample can be hybridized to the fixed sequence oligonucleotides, and then the hybridization complexes are subsequently bound to a substrate. Alternatively, the nucleic acids from the sample can be attached to a solid support prior to hybridization of the fixed sequence oligonucleotides or at the same time. Either way, following hybridization and attachment of the nucleic acids to a solid support, or alternatively following ligation of the hybridized oligonucleotides, the surface of the support can be treated to remove any unhybridized or unligated oligonucleotides, e.g., by washing or other removal methods such as degradation of oligonucleotides as discussed in Willis et al., U.S. Pat. Nos. 7,700,323 and 6,858,412. Degradation of the oligonucleotides is a preferred aspect when the two fixed sequence oligonucleotides are on the same probe such that ligation results in a circularized probe. Exonucleases may then be used to degrade non-circularized nucleic acids, including excess probes and sample DNA.

There are a number of methods that may be used to associate nucleic acids with binding pairs. For example, numerous methods may be used for labeling nucleic acids with biotin, including random photobiotinylation, end-labeling with biotin, replicating with biotinylated nucleotides, and replicating with a biotin-labeled primer.

The number of loci analyzed for each chromosome in the methods of the invention may vary from two to 20,000 or more per target genomic region analyzed. In a preferred aspect, the number of loci per target genomic region is between 48 and 1000. In another aspect, the number of loci per target genomic region is at least 100. In another aspect, the number of loci per target genomic region is at least 400. In another aspect, the number of loci per target genomic region is no more than 1000. In another aspect, the number of loci per target genomic region is at least 500 but no more than 2000.

While the embodiment illustrated in FIG. 2 uses fixed sequence oligonucleotides coupled directly to a detectable label, a label may instead be provided by a separate, labeled oligonucleotide that is hybridized to the ligation products of the fixed sequence oligonucleotides or amplicons or cleaved amplicon (as described below) thereof, to allow detection. Optionally, the labeled oligonucleotide is ligated to the capture probe following hybridization to the fixed sequence oligonucleotides or amplicons or cleaved amplicon. FIG. 3 is an illustration of one embodiment of the invention in which the fixed sequence oligonucleotides are hybridized to loci of interest, ligated, amplified and introduced to an array prior to hybridization of a labeled oligonucleotide and detection of the label. In the method depicted in FIG. 3, two sets of fixed sequence oligonucleotides 302, 304 are provided, wherein the sets comprise a first fixed sequence oligonucleotide 306, 308 each comprising sequences complementary to a selected locus 310, 312, label binding region 314, 316 and universal primer regions 318, 320; and a second fixed sequence oligonucleotide 322, 324 comprising sequences complementary to the selected locus 326, 328, a capture region 330, 332 and a universal primer region 334, 336. In many embodiments, the capture region 330, 332 comprise substantially the same sequence and will both hybridize to the same capture probe on an array. The label binding regions 314, 316 comprise sequences that are different for each set of fixed sequence oligonucleotides 302, 304 allowing differential labeling of the fixed sequence oligonucleotides associated with the loci for each target genomic region, while the capture regions 330, 332 are the same for both sets of fixed sequence oligonucleotides 302, 304 to allow for competitive hybridization of the ligation products to capture features on an array. In step 338, the sets of fixed sequence oligonucleotides 302, 304 are introduced to a sample and allowed to hybridize to loci 340, 342 of different target genomic regions. Following hybridization, unhybridized fixed sequence oligonucleotides preferably are separated from the remainder of the genetic sample (not shown).

In step 344, the sets of fixed sequence oligonucleotides 302, 304 are ligated to create ligation products 346, 348. In step 358, universal primers 350, 352, 354 and 356 are introduced to the ligation products 346, 348 which bind to the universal primer regions 318, 334, 320, and 336, respectively, and create amplicons 360, 362 each comprising capture regions 364, 366 and label binding regions 368, 370. In certain preferred embodiments, 350 and 354 have substantially the same sequence, which is complementary to both 318 and 320, and 352 and 356 have substantially the same sequence, which is complementary to both 334 and 336. The amplicons are introduced to a hybridization array 372 comprising a plurality of capture probes 374 wherein the capture regions 364, 366 of the amplicons 360, 362 hybridize to the capture probes 374. In step 378 labeled oligonucleotides 380, 382 are introduced to the array 372 where the label binding regions 368, 370 of the amplicons 360, 362 hybridize to target recognition regions 384, 386 of the labeled oligonucleotides 380, 382. Optionally, the labelled oligonucleotides are ligated to the capture probe on the array (not shown). Following hybridization of the labeled oligonucleotides, unhybridized labeled oligonucleotides preferably are separated from the array (not shown). The labels can then be detected and the loci corresponding to each target genomic region quantified to provide information on the presence and quantity of each target genomic region in the sample.

In certain embodiments, such as the embodiment shown in FIG. 3, labeled oligonucleotides are hybridized to the fixed sequence oligonucleotides, or amplicons or cleaved amplicons thereof, after the ligation products or amplicons or cleaved amplicons are hybridized to an array. In other certain embodiments, the labeled oligonucleotides are hybridized to the fixed sequence oligonucleotides, or amplicons or cleaved amplicons thereof, prior to hybridization to an array.

To facilitate hybridization of ligation products or amplicons thereof, the size of the ligation products or amplicons may be reduced prior to hybridization to an array. In certain embodiments, the ligation products are cleaved (e.g., using restriction endonucleases or other enzymatic cleaving mechanisms) to reduce the size of the ligation product to be detected, leaving, e.g., the capture region and the label binding region available for detection. Detection of a cleaved labeled ligation product or a cleaved amplicon serves as a surrogate in lieu of detecting the entire ligation product.

Reducing the size of the ligation products, amplicons and/or labeled ligation products can facilitate binding on the array, e.g., by improving hybridization kinetics and by decreasing steric hindrance. In certain embodiments, reduction in the size of the ligation products is accomplished by cleaving the ligation products or amplicons using a restriction enzyme. For example, in certain embodiments, one of the fixed sequence oligonucleotides in each set of fixed sequence oligonucleotides comprises a restriction enzyme recognition site proximal to the capture region or label binding region (or the corresponding complementary sequences thereof depending on the embodiment). A restriction enzyme can be used to cleave the ligation product at the restriction enzyme recognition site leaving the label or label binding region and the capture region available for hybridization and detection. A restriction enzyme recognition site may be located in any position that leaves the capture region and the label binding region available for detection after cleavage. For example, the restriction enzyme recognition site may be located directly next to the capture region or the label binding region or within a few bases from either of the capture region or label binding region. Preferably cleavage is carried out prior to hybridization of the labeled oligonucleotide to the ligation products or amplicons. In certain other aspects, cleavage occurs after hybridization to the array for detection.

FIG. 4 is an illustration of a specific embodiment of the invention in which the ligation product is cleaved prior to hybridization to an array. In the method depicted in FIG. 4, two sets of fixed sequence oligonucleotides 402, 404 are provided. Each set comprises a first fixed sequence oligonucleotide 406, 408 comprising sequences complementary to loci 410, 412, label binding regions 414, 416, capture regions 418, 420, universal primer regions 422, 424 and restriction enzyme recognition site regions 426, 428. The label binding regions 414, 416 comprise sequences that are different for the sets of fixed sequence oligonucleotides 402, 404 to allow differential labeling of fixed sequence oligonucleotides associated with each different target genomic region, while the capture regions 418, 420 in this embodiment are the same for both sets of fixed sequence oligonucleotides 402, 404 to allow for competitive hybridization to the capture features of a hybridization array. The restriction enzyme recognition sites 426, 428 can be the same for both sets of fixed sequence oligonucleotides 402, 404 or different for each set depending on the embodiment.

In step 442, the sets of fixed sequence oligonucleotides 402, 404 are introduced to a sample and allowed to hybridize to elected loci 444, 446. Following hybridization and/or ligation, unhybridized fixed sequence oligonucleotides preferably are separated from the remainder of the sample (not shown). In step 448, the sets of fixed sequence oligonucleotides 402, 404 are ligated to create ligation products 450, 452. In step 454, universal primers 456, 458, 460 and 462 are introduced to the ligation products 450, 452 which bind to universal primer regions 422, 438, 424, and 440, respectively, to create amplicons 464, 466 comprising label binding regions 472, 474, capture regions 468, 470 and restriction enzyme recognition sites 476, 478. In step 480, a restriction enzyme is introduced to the amplicons 464, 466 which binds to the restriction enzyme recognition site 476, 478 and cleaves the amplicons leaving a cleaved amplicon 482, 484 comprising the label binding regions 472, 474 and the capture regions 468, 470. Also at step 480, the cleaved amplicons 482, 484 are introduced to a hybridization array 486 comprising a plurality of capture probes 488 where the capture regions 468, 470 of the cleaved amplicons 482, 484 competitively hybridize to the capture probes 488. In step 492, labeled oligonucleotides 492, 494 are introduced to the array 486 where the label binding regions 472, 474 of each cleaved amplicon 482, 484 hybridize to target recognition regions 496, 497 of the labeled oligonucleotides 492, 494. Following hybridization of the labeled oligonucleotides to the cleaved amplicons, unhybridized labeled oligonucleotides preferably are separated from the array (not shown). The labels 498, 499 of the labeled oligonucleotides 492, 494 can then be detected and the cleaved amplicons corresponding to each target genomic region can be quantified to provide information on the presence and amount of the target genomic regions in the sample. Note that in FIG. 4 labeled oligonucleotides 492, 494 abut capture probes 488, and thus labeled oligonucleotides 492, 494 can be ligated to capture probes 488 to, e.g., increase binding stability. Cleaved amplicons 482, 484 can then be eliminated from the array by washing.

Figure 5:
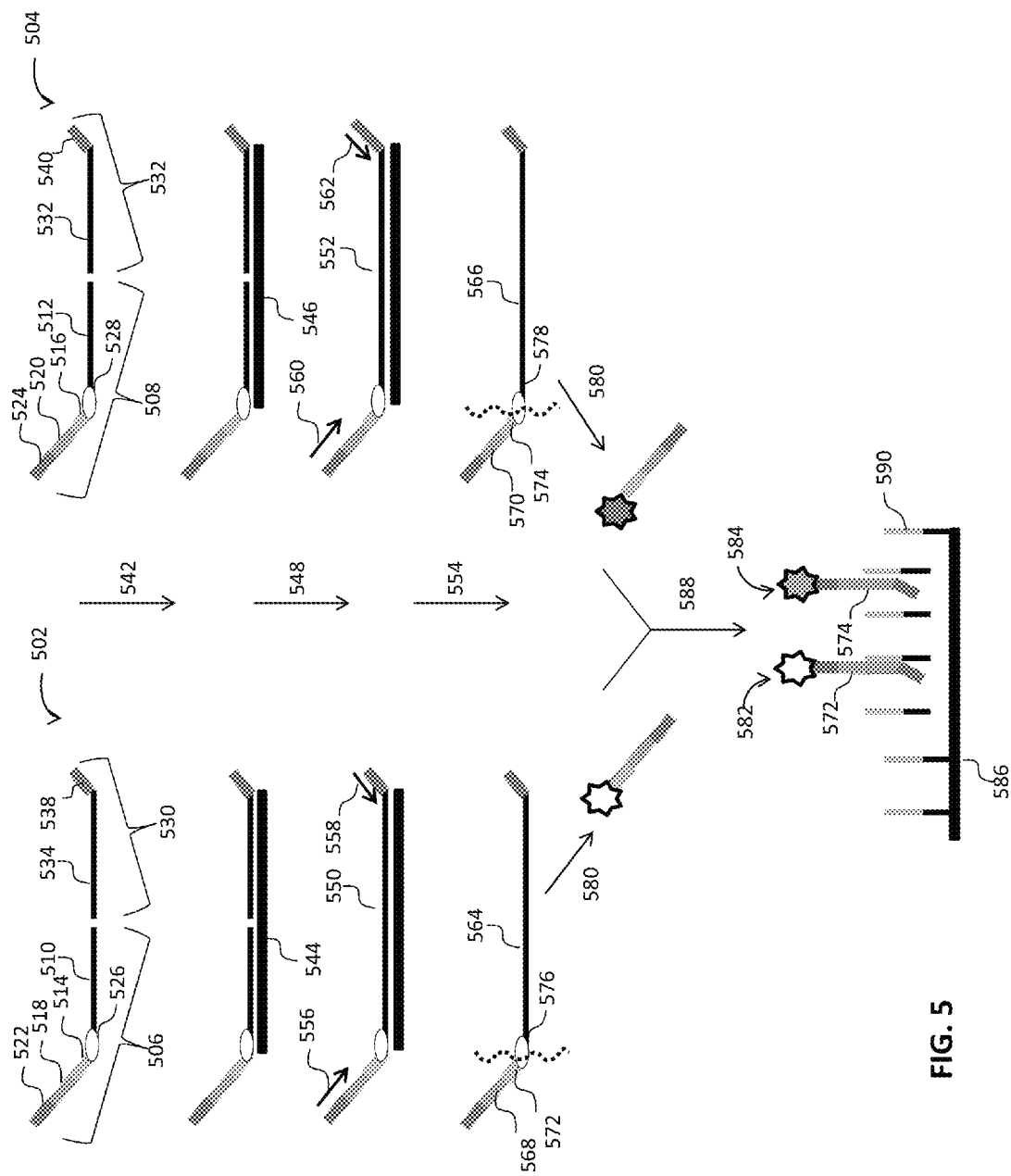
FIG. 5 illustrates yet another alternative embodiment of a method of the invention that utilizes hybridization detection of loci.

FIG. 5 is an illustration of another specific embodiment of the invention in which the ligation product is cleaved prior to hybridization to an array. In the method depicted in FIG. 5, two sets of fixed sequence oligonucleotides 502, 504 are provided. Each set comprises a first fixed sequence oligonucleotide 506, 508 comprising sequences complementary to loci 510, 512, label binding regions 514, 516, capture regions 518, 520, universal primer regions 522, 524 and restriction enzyme recognition site regions 526, 528. The label binding regions 514, 516 comprise sequences that are different for the sets of fixed sequence oligonucleotides 502, 504 to allow differential labeling of fixed sequence oligonucleotides associated with each different target genomic region, while the capture regions 518, 520 in this embodiment are the same for both sets of fixed sequence oligonucleotides 502, 504 to allow for competitive hybridization to the capture features of a hybridization array. The restriction enzyme recognition sites 526, 528 can be the same for both sets of fixed sequence oligonucleotides 502, 504 or different for each set depending on the embodiment.

In step 542, the sets of fixed sequence oligonucleotides 502, 504 are introduced to a sample and allowed to hybridize loci 544, 546. Following hybridization, unhybridized fixed sequence oligonucleotides preferably are separated from the remainder of the sample (not shown). In step 548, the sets of fixed sequence oligonucleotides 502, 504 are ligated to create ligation products 550, 552. In step 554, universal primers 556, 558, 560 and 562 are introduced to the ligation products 550, 552 which bind to universal primer regions 522, 538, 524, and 540, respectively, to create amplicons 564, 566 comprising label binding regions 572, 574, capture regions 568, 570 and restriction enzyme recognition sites 576, 578. In step 580, a restriction enzyme is introduced to the amplicons 564, 566 which binds to the restriction enzyme recognition site 576, 578 and cleaves the amplicons leaving a cleaved amplicon 582, 584 comprising the label binding regions 572, 574 and the capture regions 568, 570. The cleaved products are bound 580 to their respective labels 582, 584 and introduced to a hybridization array 586 comprising a plurality of capture probes 588 where the capture regions 568, 570 of the cleaved amplicons competitively hybridize 588 to capture probes 590.

In certain aspects of this embodiment of the invention (and as illustrated in and discussed in relation to in FIG. 4), the labeled oligonucleotides may be ligated to the capture probes of the hybridization array to increase the binding stability. This embodiment requires juxtaposition of the labelled oligonucleotide and the capture probe. The capture probes, cleaved ligation products and labeled oligonucleotides may be configured so that the labeled oligonucleotides and capture probes are hybridized adjacently to one another, or the labeled oligonucleotides and the capture probes can be extended or a gap-filling oligonucleotide may be employed as described elsewhere herein.

Detection of Copy Number Variations

As stated above, the invention provides methods to identify copy number variants of target genomic regions (relatively short genomic regions, larger genomic regions, sub-chromosomal regions and chromosomes), mutations, and polymorphisms in a sample. The present invention provides particularly powerful methods for identifying fetal chromosomal aneuploidies in maternal samples comprising both maternal and fetal DNA.

The methods of the invention can also be used to analyze multiple loci on multiple chromosomes and average the frequency of the loci from a particular chromosome together. Normalization or standardization of the frequencies can be performed for one or more target sequences.

In some aspects, the methods of the invention can be used to sum the frequencies of the loci on each chromosome for both sources in a mixed sample such as a maternal serum sample, e.g., by detecting an overall signal of a label, and then comparing the sum of the labels from the loci on one chromosome to the sum of the labels from the loci on another chromosome to determine whether a chromosomal abnormality exists. Alternatively, one can analyze subsets of loci on each chromosome to determine whether a chromosomal abnormality exists. The comparison can be made either between regions from the same chromosome or between regions from different chromosomes.

The data used to determine the frequency of the loci may exclude outlier data that appear to be due to experimental error, or that have elevated or depressed levels based on an idiopathic genetic bias within a particular sample. In one example, the data used for summation may exclude DNA regions with a particularly elevated frequency in one or more samples. In another example, the data used for summation may exclude loci that are found in a particularly low abundance in one or more samples.

Subsets of loci can be chosen randomly but with sufficient numbers to yield a statistically significant result in determining whether a chromosomal abnormality exists. Multiple analyses of different subsets of loci can be performed within a mixed sample and on different arrays to yield more statistical power. For example, if there are 100 loci for chromosome 21 and 100 loci for chromosome 18, a series of analyses could be performed that evaluate fewer than 100 loci for each of the chromosomes on different arrays. In this example, target sequences are not being selectively excluded.

The quantity of different loci detectable on certain chromosomes may vary depending upon a number of factors, including general representation of fetal loci in maternal samples, degradation rates of the different loci representing fetal loci in maternal samples, sample preparation methods, and the like.

Tandem Ligation Assay

In certain aspects, the methods of the invention employ tandem ligation methods comprising the use of first and second fixed sequence oligonucleotides that are complimentary to loci in a target genomic region, e.g., a chromosome of interest or a reference chromosome, and one or more short, bridging oligonucleotides (also called "splint" oligonucleotides or "gap" or "gap-filling" oligonucleotides) complementary to the regions of the loci between and immediately adjacent to the first and second fixed sequence oligonucleotides. Hybridization of these oligonucleotides between hybridized fixed sequence oligonucleotides on a selected locus, followed by ligation of these oligonucleotides, provides a ligation product which in turn provides a template for amplification, if desired. A tandem ligation assay tends to be more discriminating than use of a single oligonucleotide probe or use of only two fixed oligonucleotide probes, as perfect complementarity between the fixed sequence and bridging oligonucleotides and the selected locus must exist at both ligation sites for ligation to occur.

In preferred aspects, a single bridging oligonucleotide is used which hybridizes adjacently between the fixed sequence oligonucleotides in the tandem ligation methods. Alternatively in some aspects, the tandem ligation methods use sets of two fixed sequence oligonucleotides with a set of two or more bridging oligonucleotides that hybridize adjacently in the region of the nucleic acid between the region complementary to the first and second fixed sequence oligonucleotides. These bridging oligonucleotides hybridize adjacent to one another and to the fixed sequence oligonucleotides. The two fixed sequence oligonucleotides and two bridging oligonucleotides are ligated during the ligation reaction, resulting in a single ligation product which serves as a template for amplification and, ultimately for detection.

In other aspects of the invention, the method employs sets of fixed sequence oligonucleotides that bind to non-adjacent regions within a selected locus, and primer extension is utilized to create a contiguous set of hybridized oligonucleotides prior to the ligation step. Alternatively, the methods may employ sets of fixed sequence oligonucleotides, one or more bridging oligonucleotides and extension of one or more of the hybridized oligonucleotides. The combination of extension and ligation provides a ligation product which in turn serves as a template for amplification, followed by detection and quantification.

Figure 6:
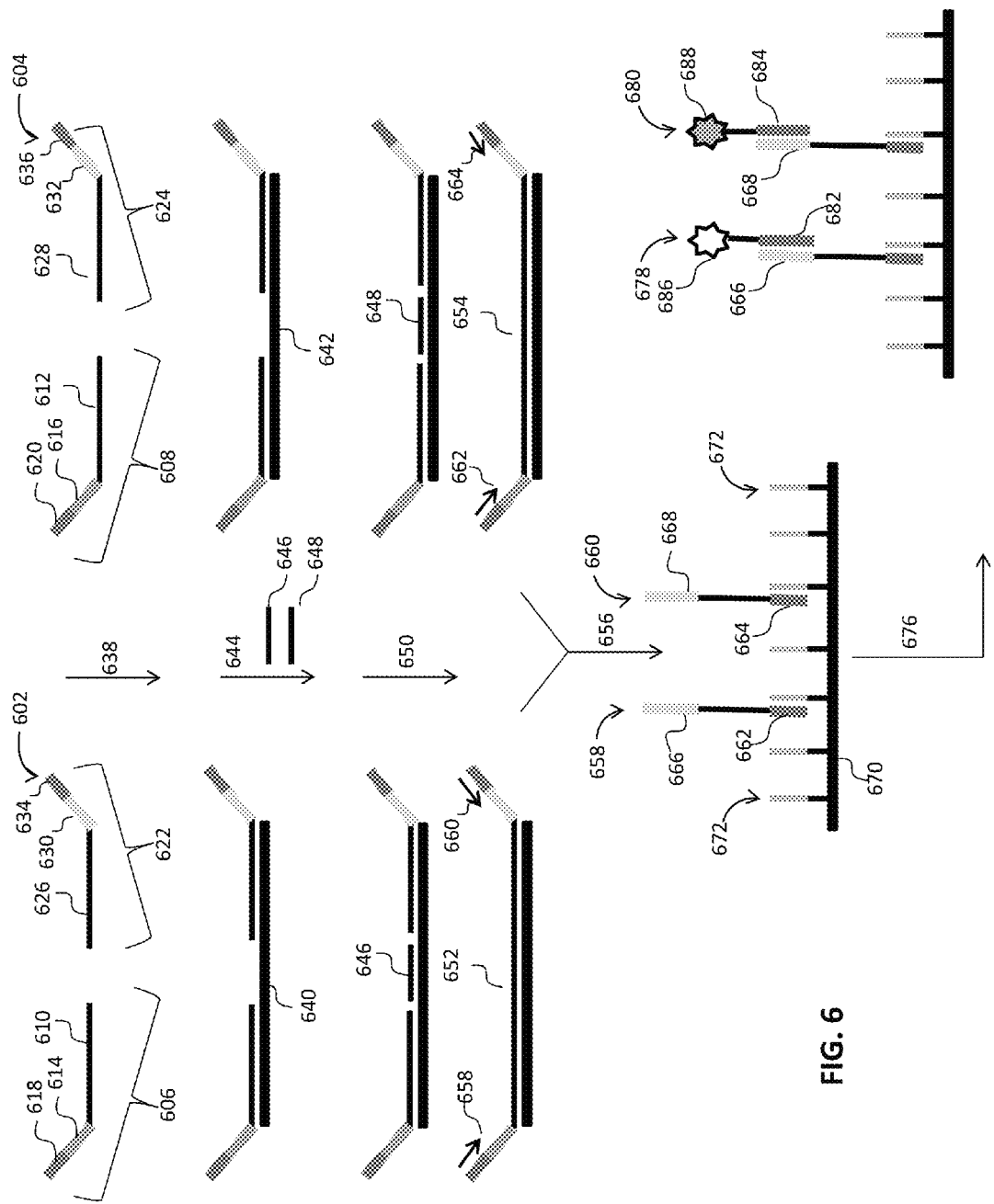
FIG. 6 illustrates another alternative embodiment of a method of the invention that utilizes bridging oligonucleotides in combination with fixed sequence oligonucleotides and hybridization detection of loci.

In a preferred aspect, the methods of the invention employ a multiplexed reaction with a set of three or more oligonucleotides for each selected locus. This general aspect is illustrated in FIG. 6 in which two sets of fixed sequence oligonucleotides 602, 604 are provided. Each set of fixed sequence oligonucleotides 602, 604 comprises first fixed sequence oligonucleotides 606, 608 each comprising a sequence complementary to a nucleic acid region of interest 610, 612, a label binding region 614, 616 and a universal primer region 618, 620, and second fixed sequence oligonucleotides 622, 624 each comprising a sequence complementary to the nucleic acid region of interest 626, 628, a capture region 630, 632 and a universal primer region 634, 636. In step 638, the sets of fixed sequence oligonucleotides 602, 604 are introduced to a sample and allowed to specifically hybridize to complementary portions of loci 640, 642 in the target genomic regions. Following hybridization, unhybridized fixed sequence oligonucleotides preferably are separated from the remainder of the genetic sample (not shown). The removal of the unhybridized fixed sequence oligonucleotides may alternatively be separated from the remainder of the genetic sample after the ligation step below. In step 644, sets of bridging oligonucleotides 646, 648 are introduced and allowed to specifically hybridize to the region of the loci between the first fixed sequence oligonucleotide 606, 608 and second fixed sequence oligonucleotide 622, 624. Alternatively, the bridging oligonucleotides 646, 648 can be introduced simultaneously with the fixed sequence oligonucleotides.

In step 650, the sets of fixed sequence oligonucleotides 602, 604 and bridging oligonucleotides 630, 632 are ligated to create ligation products 652, 654 complementary to the loci 640, 642. Also, in step 650, universal primers 658, 660, 662 and 664 are introduced to the ligation products 652, 654 where the universal primers bind to the universal primer regions 618, 634, 620, and 636, respectively, and amplify the ligation products to create amplicons 678, 680 comprising label binding regions 666, 668 and capture regions 662, 664. In certain preferred embodiments, universal primers 658 and 662 have substantially the same sequence, which is complementary to both 618 and 620, and universal primers 660 and 664 have substantially the same sequence, which is complementary to both 634 and 636. The amplicons 678, 680 are introduced to a hybridization array 670 comprising a plurality of capture probes 672 wherein the capture regions 662, 664 of the amplicons 658, 660 competitively hybridize to target capture regions 674 on the capture probes 672. In step 676, target recognition regions 682, 684 of the labeled oligonucleotides 688, 690 specifically hybridize to the label binding regions 666, 668 of the amplicons 678, 680. Following hybridization of the labeled oligonucleotides, unhybridized labeled oligonucleotides preferably are removed from the array (not shown). The labels 686, 688 of the labeled oligonucleotides 688, 690 can then be detected and the loci optionally quantified to provide information on the presence and amount of each genomic region in the genetic sample.

In certain aspects, the bridging oligonucleotides can be composed of a mixture of oligonucleotides with degeneracy in each of the positions, so that the mixture of bridging oligonucleotides will be compatible with all reactions in the multiplexed assay requiring a bridging of a given length. In one example the bridging oligonucleotide is a randomer, where all combinations of the bridging oligonucleotide are synthesized. As an example, in the case where a 5-base oligonucleotide is used, the number of unique bridging oligonucleotide s would be 4^5=1024. This would be independent of the number of targeted regions since all possible bridging oligonucleotide s would be present in the reaction. In another aspect, the bridging oligonucleotides can be of various lengths so that the mixture of oligonucleotides is compatible with ligation reactions requiring bridging oligonucleotides of different lengths.

In yet another aspect, the bridging oligonucleotide can have degeneracy at specific positions—i.e., known polymorphic sites—and the tandem ligation reactions are restricted to those that require a specific sequence provided at the polymorphic site.

In another example, the bridging oligonucleotide is specific, synthesized to match the sequences in the gap. As an example, in the case where a 5-base oligonucleotide is used, the number of unique oligonucleotides provided in the assay would be equal to or less than the number of loci. A number of bridging oligonucleotides less than the number of loci could be achieved if the gap sequence was shared between two or more loci. In one aspect of this example, one might purposefully choose loci and especially the gap sequences such that there was as much identical overlap as possible in the gap sequences, minimizing the number of bridging oligonucleotides necessary for the multiplexed reaction.

In another aspect, the sequences of the bridging oligonucleotides are designed and the loci are selected so that all loci share the same base(s) at each end of the bridging oligonucleotide. For instance, one might choose loci and their gap location such that all of the gaps shared an "A" base at the first position and a "G" base at the last position of the gap. Any combination of a first and last base could be utilized, based upon factors such as the genome investigated, the likelihood of sequence variation in that area, and the like. In a specific aspect of this example, the bridging oligonucleotides can be synthesized by random degeneracy of bases at the internal positions of the bridging oligonucleotide, with nucleotides specific at the first and last position of the bridging oligonucleotide. In the case of a 5-mer, the second, third and fourth positions would be degenerate, and the two specific nucleotides at the end of the bridging oligonucleotide would be fixed. In this case, the number of unique bridging oligonucleotides would be 4^3=64.

In the human genome the frequency of the dinucleotide CG is much lower than expected by the respective mononucleotide frequencies. This presents an opportunity to enhance the specificity of an assay with a particular mixture of bridging oligonucleotides. In this aspect, the bridging oligonucleotides may be selected to have a 5' G and a 3' C. This base selection allows each oligonucleotide to have a high frequency in the human genome but makes it a rare event for two bridging oligonucleotides to hybridize adjacent to each other. The probability is then reduced that multiple oligonucleotides are ligated in locations of the genome that are not targeted in the assay.

In certain aspects, the bridging oligonucleotide is added to the reaction after the sets of fixed sequence oligonucleotides have been hybridized, and following the optional removal of all unhybridized fixed sequence oligonucleotides. The conditions of the hybridization reaction preferably are optimized near the $T_m$ of the bridging oligonucleotide to prevent erroneous hybridization of oligonucleotides that are not fully complementary to the nucleic acid region. If the bridging oligonucleotides have a $T_m$ significantly lower than the fixed sequence oligonucleotides, the bridging oligonucleotide is preferably added as a part of the ligase reaction.

The advantage of using short bridging oligonucleotides is that ligation on either end would likely occur only when all bases of the bridging oligonucleotide match the gap sequence. A further advantage of using short bridging oligonucleotides is that the number of different bridging oligonucleotides necessary could be less than the number of loci, raising the oligonucleotides' effective concentration to allow perfect matches to happen faster. Fewer numbers of bridging oligonucleotides provides the advantages of cost savings and quality control. The advantages of using fixed first and last bases and random bases in between include the ability to utilize longer bridging oligonucleotides for greater specificity while reducing the number of total bridging oligonucleotides in the reaction.

Detection of Polymorphisms

In certain aspects, the methods of the invention detect one or more target genomic regions that comprise a polymorphism. In some embodiments, this methodology is not necessarily designed to identify a particular allele, e.g., as maternal versus fetal, but rather to ensure that different alleles corresponding to loci in a target genomic region are included in the quantification methods of the invention. In certain aspects, however, it may be desirable to both use allelic information to count all loci in the target genomic region as well as to use the allelic information, e.g., to calculate the amount of fetal DNA contained within a maternal sample, or identify the percent of alleles with a particular mutation in a genetic sample from a cancer patient. Thus, the methods of the invention are intended to encompass both mechanisms for detection of SNP-containing loci for direct determination of copy number variation through quantification as well as detection of SNPs for ensuring overall efficiency of the assay.

Thus, in a particular aspect of the invention, allelic discrimination is provided through the fixed sequence oligonucleotides or through the bridging oligonucleotides used for detection of the loci. In such embodiments, the label binding region may serve as an allele index that is embedded in either the first fixed sequence oligonucleotide or the second fixed sequence oligonucleotide in a set. In certain specific aspects, an allele index (e.g., label binding region) is present on both the first and second fixed sequence oligonucleotides to detect two or more polymorphisms within the loci. The number of fixed sequence oligonucleotides used in such aspects can correspond to the number of possible alleles being assessed for a selected locus, and detection of a label associated with the allele index can detect presence, amount or absence of a specific allele in a genetic sample.

Figure 7:
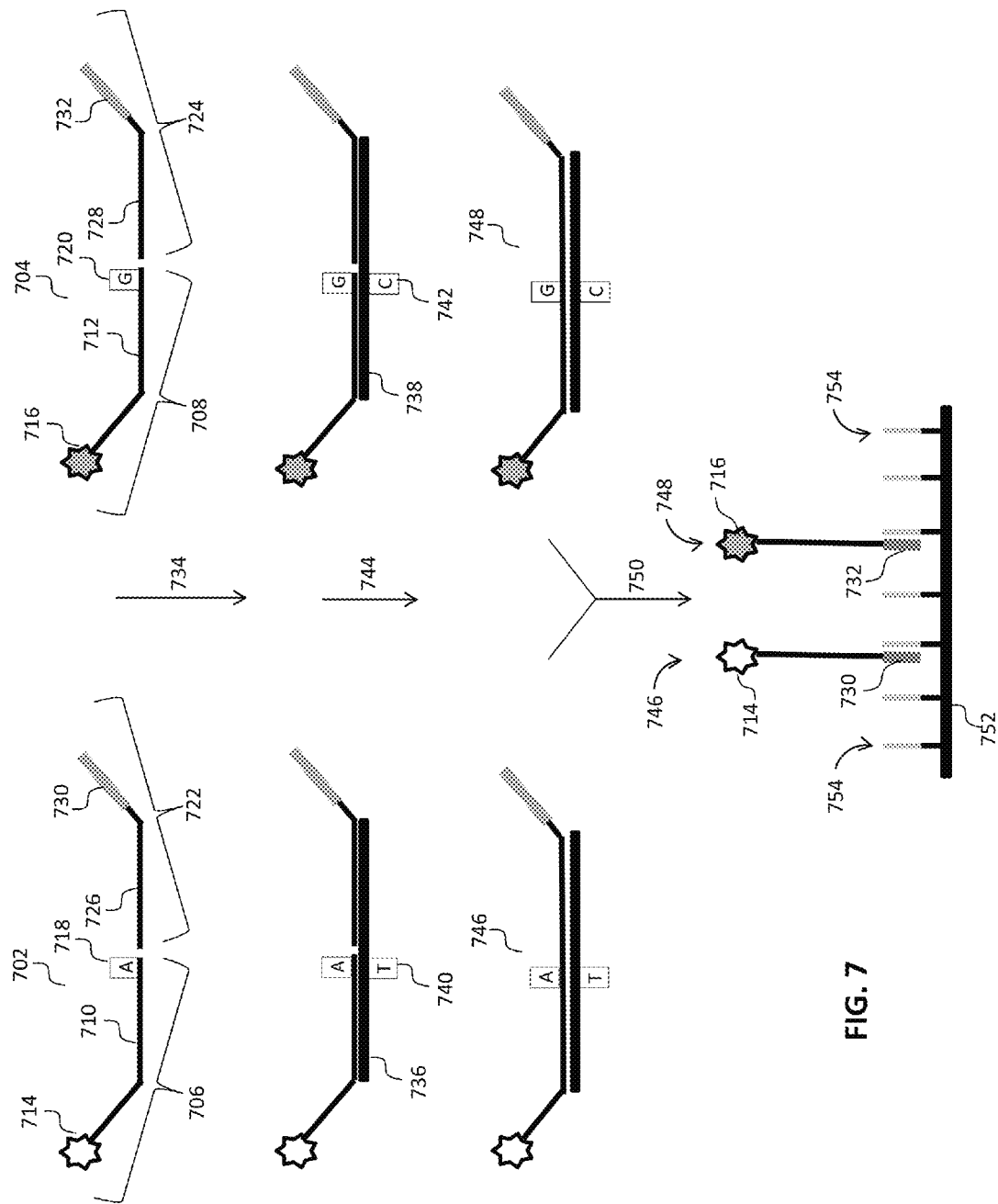
FIG. 7 illustrates another alternative embodiment of a method of the invention that utilizes hybridization detection of loci to detect polymorphisms.

FIG. 7 illustrates one aspect of the invention in which polymorphisms are detected using competitive hybridization to an array. In FIG. 7, two sets of fixed sequence oligonucleotides 702, 704 are provided in which the first fixed sequence oligonucleotide 706, 708 of each set comprises a sequence that is complementary to a locus of interest 710, 712 comprising for example an A/T or G/C SNP, respectively and a label 714, 716. The second fixed sequence oligonucleotide 722, 724 comprises a sequence that is complementary to the selected locus 726, 728 and a capture region 730, 732. In some embodiments, fixed sequence oligonucleotide 706 is the same as fixed sequence oligonucleotide 708 except for SNPs 718 and 720 and labels 714 and 716, respectively; and fixed sequence oligonucleotide 722 is the same as fixed sequence oligonucleotide 724. That is, the difference between the sets of fixed sequence oligonucleotides is the SNP interrogated and the label that corresponds to the SNP. In step 734, the sets of fixed sequence oligonucleotides 702, 704 are introduced to the sample and allowed to specifically hybridize to locus of interest 736, 738 comprising SNPs 740, 742. Following hybridization or ligation, unhybridized fixed sequence oligonucleotides preferably are separated from the remainder of the genetic sample (not shown). In step 744, the sets fixed sequence oligonucleotides 702, 704 are ligated to create ligation products 746, 748. It is important to note that in this embodiment the ligation is allele-specific as long as the allele-specific nucleotide is close to the ligation junction. Typically, the allele-specific nucleotide must be within 5 nucleotides of the ligated end; however, in preferred aspects, the allele-specific nucleotide is the terminal base.

In step 750, the ligation products 746, 748 are introduced to a hybridization array 752 comprising a plurality of capture probes 754 where the capture regions 730, 732 of the ligation products 746, 748 hybridize to the capture probes 754. Following hybridization of the ligation products, unhybridized ligation products preferably are separated from the remainder of the genetic sample (not shown). The labels 714, 716 can then be detected and alleles specific to the loci corresponding to each target genomic region are quantified to provide information on the presence and amount each allele and target genomic region in the genetic sample.

Figure 8:
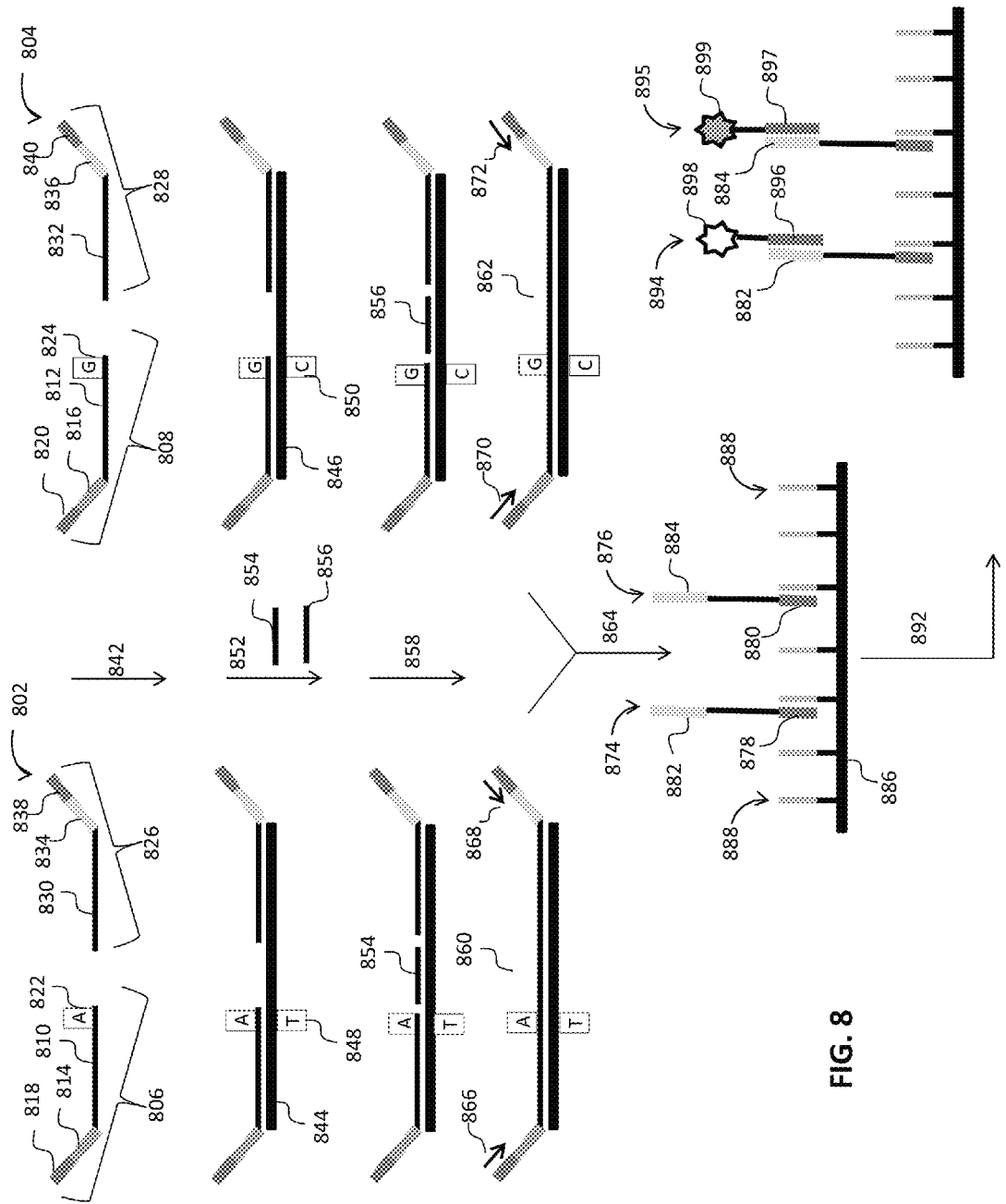
FIG. 8 illustrates another alternative embodiment of a method of the invention that utilizes hybridization detection of loci to detect polymorphisms.

In another embodiment, the allele-specific nucleotide is disposed in the first and/or second fixed sequence oligonucleotides and bridging oligonucleotides are used to create ligation products. FIG. 8 illustrates this aspect of the invention. In FIG. 8, two sets of fixed sequence oligonucleotides 802, 804 are provided, where both sets of fixed sequence oligonucleotides are configured to interrogate different SNPs at the same selected locus. The first fixed sequence oligonucleotides 806, 808 of each set comprise a sequence that is complementary to a selected locus 810, 812 comprising for example an NT or G/C SNP, respectively, a label binding region 814, 816, and a universal primer region 818, 820; and second fixed sequence oligonucleotides 826, 828 each comprising sequences that are complementary to a selected locus 830, 832, capture region 834, 836 and universal primer regions 838, 840. In the polymorphic assays, second fixed sequence oligonucleotides 826 and 828 have substantially the same sequence and first fixed sequence oligonucleotides 806, 808 have substantially the same sequence except for the SNP site and the label binding regions 814, 816. In step 842, the sets of fixed sequence oligonucleotides 802, 804 are introduced to the sample and are allowed to hybridize to the loci 844, 846 comprising SNPs 848, 850. Following hybridization, unhybridized fixed sequence oligonucleotides preferably are separated from the remainder of the genetic sample (not shown).

In step 852, a set of bridging oligonucleotides 854, 856 are introduced to the sample and allowed to hybridize to the locus 844, 846 between the first and second fixed oligonucleotides of each set. In a preferred embodiment, 854 and 856 have substantially the same sequence. In step 858, the hybridized fixed sequence oligonucleotides and hybridized bridging oligonucleotides are ligated to create ligation products 860, 862. In step 864, universal primers 866, 868, 870 and 872 are introduced to the ligation products 860, 862 which bind to universal primer regions 818, 838, 820, and 840, respectively and amplify the ligation products 860, 862 to produce amplicons 874, 876 comprising label binding regions 882, 884 and capture regions 878, 880. The amplicons are introduced to a hybridization array 886 comprising capture probes 888 where the capture regions 878, 880 of the amplicons 874, 876 hybridize to the capture probes 888. In step 892, labeled oligonucleotides 894, 895 are introduced to the hybridization array 886 under conditions that allow the target recognition regions 896, 897 of the labeled oligonucleotides 894, 895 to selectively hybridize to the label binding regions 882, 884 of the amplicons 874, 876. Following hybridization of the labeled oligonucleotides, unhybridized labeled oligonucleotides preferably are removed from the array (not shown). The labels 898, 899 can then be detected and alleles corresponding to the loci corresponding to the target genomic regions quantified to provide information on the presence and amount of the alleles at loci and the target genomic regions in the genetic sample.

In certain aspects of the invention, allelic discrimination is provided through the bridging oligonucleotide. In this aspect, the bridging oligonucleotide is located over a SNP, preferably located close enough to one end of a ligation junction so as to provide allelic-specificity.

Figure 9:
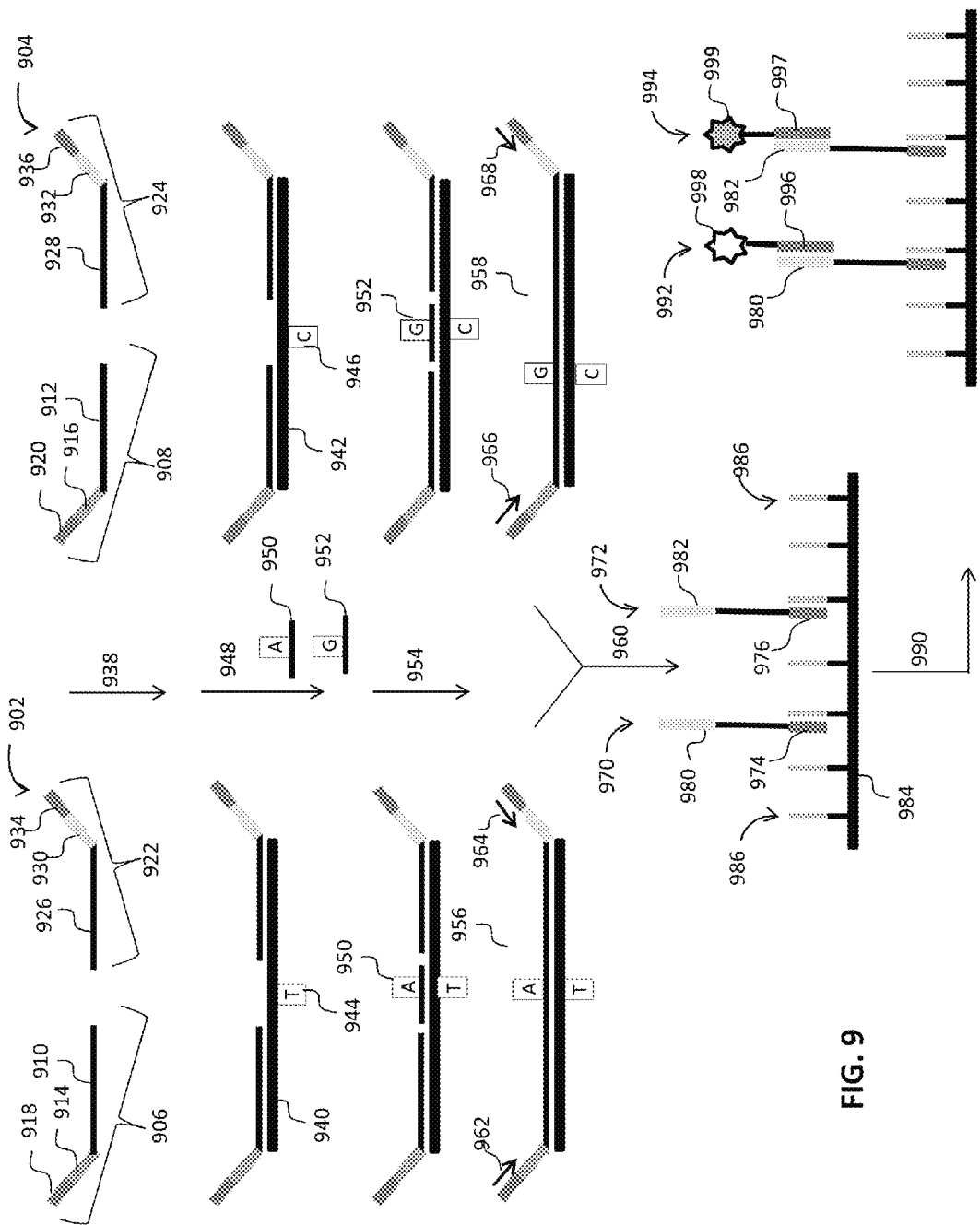
FIG. 9 illustrates another alternative embodiment of a method of the invention that utilizes hybridization detection of nucleic acid regions to detect polymorphisms.

In one example, both allele bridging oligonucleotide variants are present in the same reaction mixture and allele detection results from subsequent hybridization of associated labels to hybridization arrays. FIG. 9 illustrates this aspect.

In FIG. 9, two sets of fixed sequence oligonucleotides 902, 904 are provided where both sets of fixed sequence oligonucleotides are configured to interrogate the same selected locus and are the same except for the label binding region. In this embodiment, the bridging oligonucleotide interrogates the SNP, and the assay must be performed in two separate vessels at least until after the ligation step has taken place. The first fixed sequence oligonucleotides 906, 908 in each set comprise sequences that are complementary to a locus 910, 912, a capture region 914, 916 and universal primer region 918, 920. The second fixed sequence oligonucleotides 922, 924 of each set comprise sequences that are complementary to the locus 926, 928, a label binding region 930, 932 region and a universal primer region 934, 936. In step 938, the sets of fixed sequence oligonucleotides 902, 904 are introduced to the sample under conditions that allow each set 902, 904 to specifically hybridize to the locus 940, 942 wherein the selected locus comprises a SNP 944, 946. Following hybridization (or alternatively following ligation) of the first and second fixed sequence oligonucleotides, unhybridized fixed sequence oligonucleotides preferably are separated from the remainder of the genetic sample (not shown). In step 948, bridging oligonucleotides 950, 952 corresponding to an A/T SNP or a G/C SNP are introduced and allowed to bind to the region of the locus 940, 942 between the first and second fixed sequence oligonucleotides. Alternatively, the bridging oligonucleotides can be introduced to the sample simultaneously with the fixed sequence oligonucleotides.

In step 954, the hybridized fixed sequence oligonucleotides and bridging oligonucleotides are ligated to create ligation products 956, 958. At this point the two separate assays optionally can be combined into a single vessel but need not be. In step 960, universal amplification primers 962, 964, 966 and 968 are introduced to the ligation products 956, 958 where the universal primers bind to universal primer regions 918, 934, 920, and 936, respectively, and amplify the ligation products 956, 958 to produce amplicons 970, 972, each comprising a label binding region 980, 982 and a capture region 974, 976. The amplicons 970, 972 are introduced to a hybridization array 984 comprising a plurality of capture probes 986 wherein the capture regions 974, 976 of the amplicons 970, 972 competitively hybridize to the capture probes 986. In step 990, labeled oligonucleotides 992, 994 are introduced to the array 984 where target recognition regions 996, 997 of the labeled oligonucleotides 992, 994 hybridize to label binding regions 980, 982 of the amplicons 970, 972. Following hybridization of the labeled oligonucleotides, unhybridized labeled oligonucleotides preferably are removed from the array (not shown). The labels 998, 999 can then be detected and alleles corresponding to the loci corresponding in turn to the target genomic regions are quantified to provide information on the presence and amount of each allele and target genomic region in the sample.

Additional Embodiments

Figure 10:
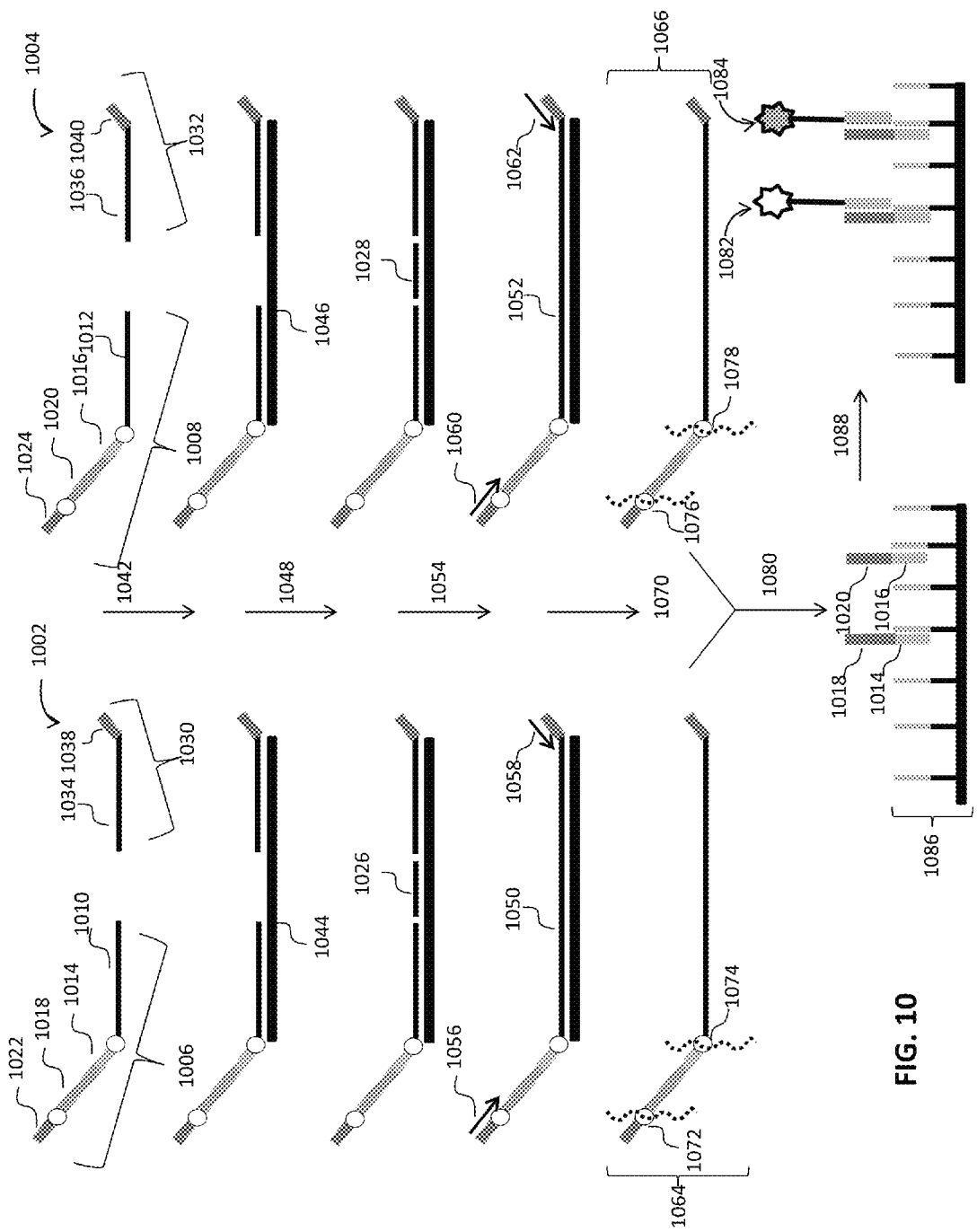
FIG. 10 illustrates a method of the invention that utilizes hybridization detection of nucleic acid regions with a bridging oligonucleotide and dual cleavage.

FIG. 10 is an illustration of another specific embodiment of the invention in which bridging oligonucleotides are used and the ligation products are dually cleaved prior to hybridization to an array. In the method depicted in FIG. 10, two sets of fixed sequence oligonucleotides 1002, 1004 are provided. Each set comprises a first fixed sequence oligonucleotide 1006, 1008 comprising sequences complementary to loci 1010, 1012, label binding regions 1018, 1020, capture regions 1014, 1016, universal primer regions 1022, 1024 and restriction enzyme recognition site regions 1026, 1028. The label binding regions 1018, 1020 comprise sequences that are different for the sets of fixed sequence oligonucleotides 1002, 1004 to allow differential labeling of fixed sequence oligonucleotides associated with each different target genomic region, while the capture regions 1014, 1016 in this embodiment are the same for both sets of fixed sequence oligonucleotides 1002, 1004 to allow for competitive hybridization to the capture features of a hybridization array. The restriction enzyme recognition sites 1026, 1028 can be the same for both cleavage sites on each fixed sequence oligonucleotide, and/or the same for the different sets of fixed sequence oligonucleotides 1002, 1004 depending on the embodiment. There is also a second fixed sequence oligonucleotide 1030, 1032 in each set, where each second fixed sequence oligonucleotide comprises a sequence complementary to the loci 1034, 1036 and a universal primer region 1038, 1040.

In step 1042, the sets of fixed sequence oligonucleotides 1002, 1004 are introduced to a sample and allowed to hybridize loci 1044, 1046. Following hybridization (or alternatively ligation), unhybridized fixed sequence oligonucleotides preferably are separated from the remainder of the sample (not shown). In step 1048, a bridging oligonucleotide 1026, 1028 is added to each set and hybridized adjacently between the hybridized fixed sequence oligonucleotides. At step 1054, the sets of oligonucleotides are ligated to create ligation products 1050, 1052. In step 1054, universal primers 1056, 1058, 1060 and 1062 are introduced to the ligation products 1050, 1052 which bind to universal primer regions 1022, 1038, 1024, and 1040, respectively, to create amplicons 1064, 1066 comprising label binding regions 1018, 1020, capture regions 1014, 1016, and restriction enzyme recognition sites 1072, 1074, 1076, and 1078. In step 1070, one or more restriction enzymes are introduced to the amplicons 1064, 1066 and the amplicons are dually cleaved to create a cleaved amplicon comprising the label binding regions 1018, 1020 and the capture regions 1014, 1016. The cleaved products are introduced to a hybridization array 1086 comprising a plurality of capture probes 1088 where the capture regions 1014, 1016 of the cleaved amplicons competitively hybridize to capture probes 1090. The hybridized capture regions are then introduced 1088 to the labeled oligonucleotides 1082, 1084, which bind to complementary sequences on the cleaved products and are detected.

Figure 11:
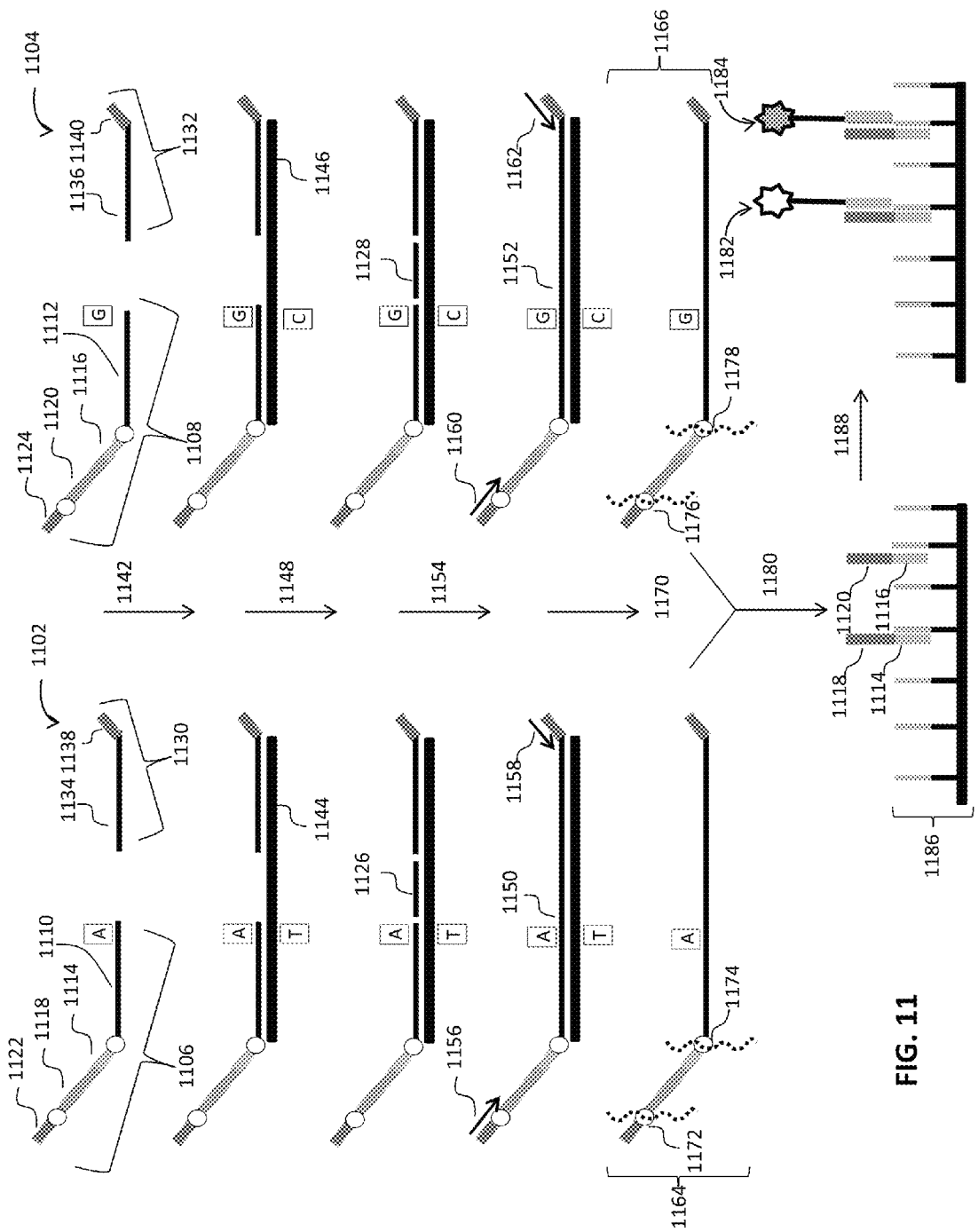
FIG. 11 of a method of the invention that utilizes hybridization detection of nucleic acid regions with a bridging oligonucleotide and dual cleavage to detect polymorphisms.

FIG. 11 is an illustration of another specific embodiment of the invention in which bridging oligonucleotides are used to identify different alleles in the same locus and the ligation products are dually cleaved prior to hybridization to an array. In the method depicted in FIG. 11, two sets of fixed sequence oligonucleotides 1102, 1104 are provided for a single locus having a possible polymorphism. Each set comprises a first fixed sequence oligonucleotide 1106, 1108 comprising sequences complementary to one allele of the selected locus 1110, 1112, label binding regions 1118, 1120, capture regions 1114, 1116, universal primer regions 1122, 1124 and restriction enzyme recognition site regions 1126, 1128. The label binding regions 1118, 1120 comprise sequences that are different for the sets of fixed sequence oligonucleotides 1102, 1104 to allow differential labeling of fixed sequence oligonucleotides associated with each different allele, while the capture regions 1114, 1116 in this embodiment are the same for both sets of fixed sequence oligonucleotides 1102, 1104 to allow for competitive hybridization to the capture features of a hybridization array. The restriction enzyme recognition sites 1126, 1128 can be the same for both cleavage sites on each fixed sequence oligonucleotide, and/or the same for the different sets of fixed sequence oligonucleotides 1102, 1104 depending on the embodiment. There is also a second fixed sequence oligonucleotide 1130, 1132 in each set, where each second fixed sequence oligonucleotide comprises a sequence complementary to the selected locus 1134, 1136 and a universal primer region 1138, 1140.

In step 1142, the sets of fixed sequence oligonucleotides 1102, 1104 are introduced to a sample and allowed to hybridize to the selected locus 1144, 1146. Following hybridization (or alternatively ligation), unhybridized fixed sequence oligonucleotides preferably are separated from the remainder of the sample (not shown). In step 1148, a bridging oligonucleotide 1126, 1128 is added to each set and hybridized adjacently between the hybridized fixed sequence oligonucleotides. At step 1154, the sets of oligonucleotides are ligated to create ligation products 1150, 1152. In step 1154, universal primers 1156, 1158, 1160 and 1162 are introduced to the ligation products 1150, 1152 which bind to universal primer regions 1122, 1138, 1124, and 1140, respectively, to create amplicons 1164, 1166 comprising label binding regions 1118, 1120, capture regions 1114, 1116, and restriction enzyme recognition sites 1172, 1174, 1176, and 1178. In step 1170, one or more restriction enzymes are introduced to the amplicons 1164, 1166 and the amplicons dually cleaved to create a cleaved amplicon comprising the label binding regions 1118, 1120 and the capture regions 1114, 1116. The cleaved products are introduced to a hybridization array 1186 comprising a plurality of capture probes 1188 where the capture regions 1118, 1120 of the cleaved amplicons competitively hybridize to capture probes 1190. The hybridized capture regions are then introduced 1188 to the labeled oligonucleotides 1182, 1184, which bind to complementary sequences on the cleaved products and are detected to differentiate between the different alleles of the locus.

Figure 12:
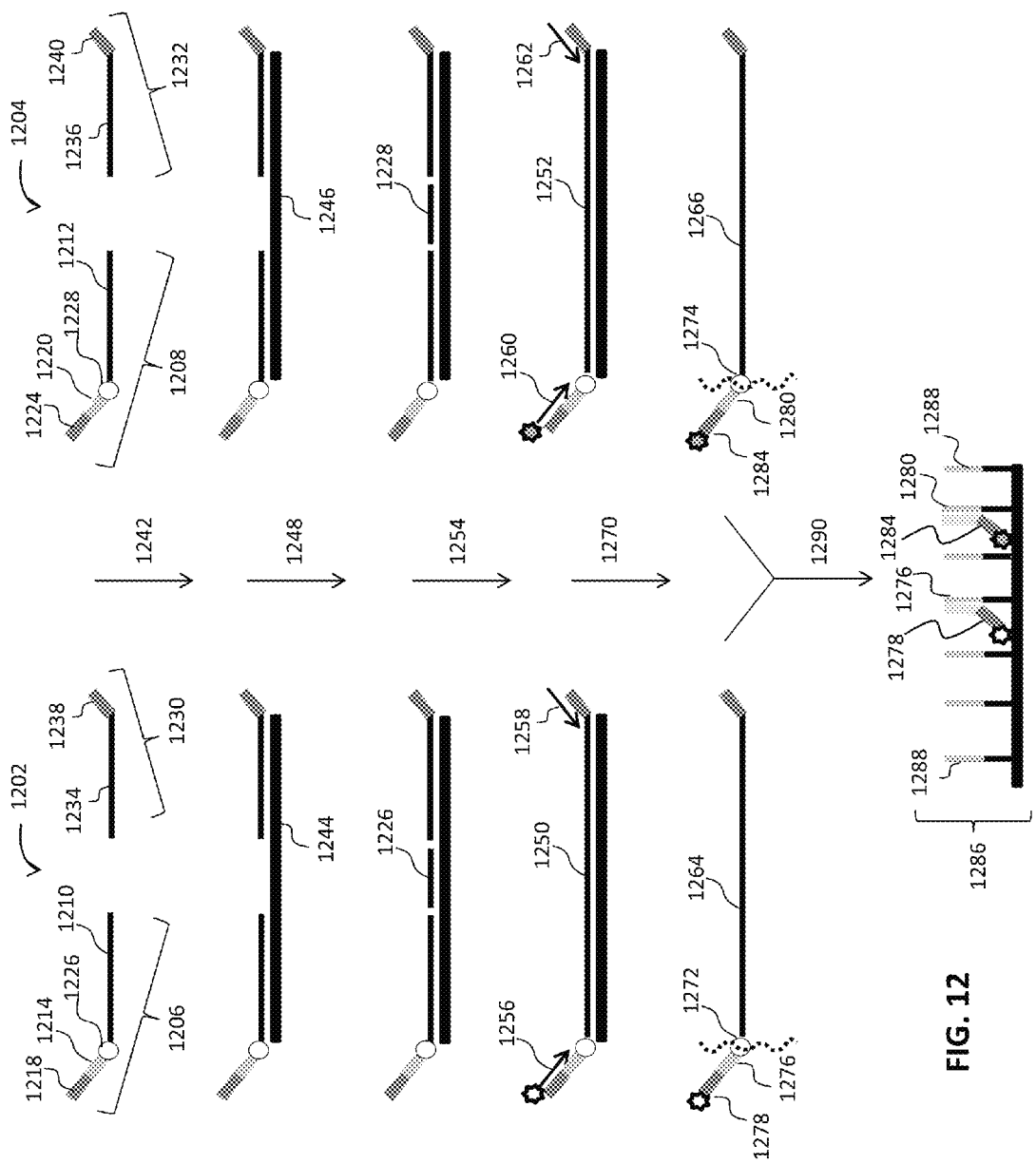
FIG. 12 illustrates a method of the invention that utilizes hybridization detection of nucleic acid regions resulting from a single cleavage event and employing differentially labeled universal primers.

FIG. 12 is an illustration of another specific embodiment of the invention in which bridging oligonucleotides are used and the ligation products are cleaved prior to hybridization to an array. In this embodiment, the primers used to amplify the ligation products are differentially labeled. In the method depicted in FIG. 12, two sets of fixed sequence oligonucleotides 1202, 1204 are provided. Each set comprises a first fixed sequence oligonucleotide 1206, 1208 comprising sequences complementary to loci 1210, 1212, primer binding regions 1218, 1224 (which are different), capture regions 1214, 1220, and restriction enzyme recognition site regions 1226, 1228. The primer binding regions 1218, 1224 comprise sequences that are different for the sets of fixed sequence oligonucleotides 1202, 1204 to allow differential labeling of fixed sequence oligonucleotides associated with each different target genomic region, while the capture regions 1214, 1220 in this embodiment are the same for both sets of fixed sequence oligonucleotides 1202, 1204 to allow for competitive hybridization to the capture features of a hybridization array. The restriction enzyme recognition sites 1226, 1228 can be the same for both cleavage sites on each fixed sequence oligonucleotide, and/or the same for the different sets of fixed sequence oligonucleotides 1302, 1304 depending on the embodiment. There is also a second fixed sequence oligonucleotide 1230, 1232 in each set, where each second fixed sequence oligonucleotide comprises a sequence complementary to the loci 1234, 1236 and a primer region 1238, 1240.

In step 1242, the sets of fixed sequence oligonucleotides 1202, 1204 are introduced to a sample and allowed to hybridize loci 1244, 1246. Following hybridization (or alternatively ligation), unhybridized fixed sequence oligonucleotides preferably are separated from the remainder of the sample (not shown). In step 1248, a bridging oligonucleotide 1226, 1228 is added to each set and hybridized adjacently between the hybridized fixed sequence oligonucleotides. At step 1254, the sets of oligonucleotides are ligated to create ligation products 1250, 1252. In step 1254, primers 1256, 1258, 1260 and 1262 are introduced to the ligation products 1250, 1252 which bind to primer regions 1218, 1238, 1224, and 1240, respectively, to create amplicons 1264, 1266 comprising primer binding regions 1278, 1284, capture regions 1276, 1280, and restriction enzyme recognition sites 1272 and 1274. Primers 1256 and 1260 are differentially labeled thus allowing for differentiation between amplicons from the different loci once the amplicons are hybridized to an array. In step 1270, one or more restriction enzymes are introduced to the amplicons 1264, 1266 and the amplicons are cleaved to create a cleaved amplicon comprising the primer binding regions 1278, 1284 and the capture regions 1276, 1280. The cleaved products are introduced to a hybridization array 1286 at step 1290 comprising a plurality of capture probes 1288 where the capture regions 1276, 1280 of the cleaved amplicons competitively hybridize to capture probes 1288.

Figure 13:
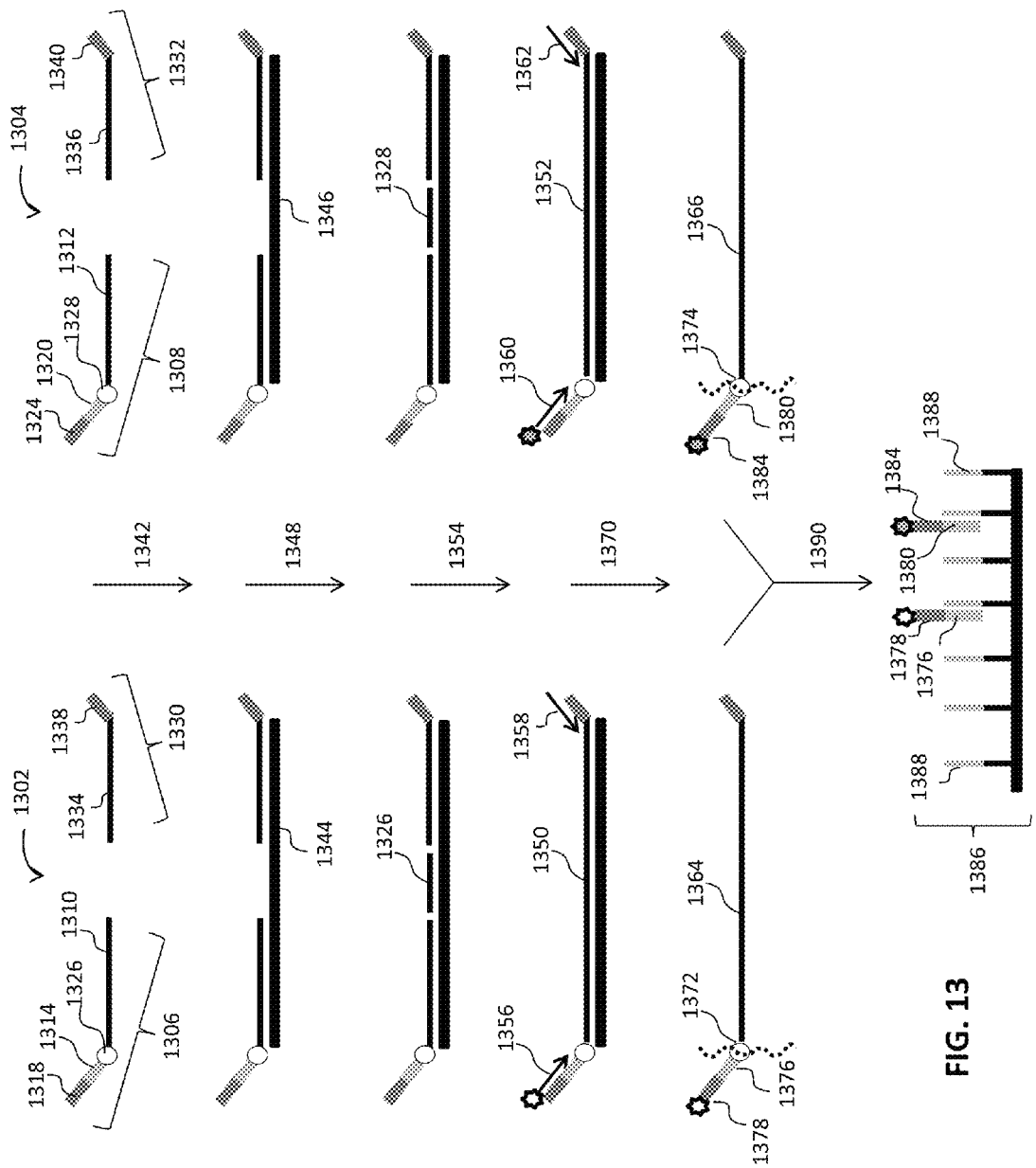
FIG. 13 illustrates an alternative method to that illustrated in FIG. 12 also utilizing hybridization detection of nucleic acid regions resulting from a single cleavage event and employing differentially labeled universal primers.

FIG. 13 is an illustration of another specific embodiment of the invention in which bridging oligonucleotides are used and the ligation products are cleaved prior to hybridization to an array. FIG. 13 illustrates an embodiment very similar to that in FIG. 12. In this embodiment, the primers used to amplify the ligation products are differentially labeled. In the method depicted in FIG. 13, two sets of fixed sequence oligonucleotides 1302, 1304 are provided. Each set comprises a first fixed sequence oligonucleotide 1306, 1308 comprising sequences complementary to loci 1310, 1312, primer binding regions 1318, 1324 (which are different), capture regions 1314, 1320 (which are the same), and restriction enzyme recognition site regions 1326, 1328. The primer binding regions 1318, 1324 comprise sequences that are different for the sets of fixed sequence oligonucleotides 1302, 1304 to allow differential labeling of fixed sequence oligonucleotides associated with each different target genomic region, while the capture regions 1314, 1320 in this embodiment are the same for both sets of fixed sequence oligonucleotides 1302, 1304 to allow for competitive hybridization to the capture features of a hybridization array. The restriction enzyme recognition sites 1326, 1328 can be the same for both cleavage sites on each fixed sequence oligonucleotide, and/or the same for the different sets of fixed sequence oligonucleotides 1302, 1304 depending on the embodiment. There is also a second fixed sequence oligonucleotide 1330, 1332 in each set, where each second fixed sequence oligonucleotide comprises a sequence complementary to the loci 1334, 1326 and a primer region 1338, 1340.

In step 1342, the sets of fixed sequence oligonucleotides 1302, 1304 are introduced to a sample and allowed to hybridize loci 1344, 1346. Following hybridization (or alternatively ligation), unhybridized fixed sequence oligonucleotides preferably are separated from the remainder of the sample (not shown). In step 1348, a bridging oligonucleotide 1326, 1328 is added to each set and hybridized adjacently between the hybridized fixed sequence oligonucleotides. At step 1354, the sets of oligonucleotides are ligated to create ligation products 1350, 1352. In step 1354, primers 1356, 1358, 1360 and 1362 are introduced to the ligation products 1350, 1352 which bind to primer regions 1318, 1338, 1324, and 1340, respectively, to create amplicons 1364, 1366 comprising primer binding regions 1378, 1384, capture regions 1376, 1380, and restriction enzyme recognition sites 1372 and 1374. Primers 1356 and 1360 are differentially labeled thus allowing for differentiation between amplicons from the different loci once the amplicons are hybridized to an array. In step 1370, one or more restriction enzymes are introduced to the amplicons 1364, 1366 and the amplicons are cleaved to create a cleaved amplicon comprising the primer binding regions 1378, 1384 and the capture regions 1376, 1380. The cleaved products are introduced to a hybridization array 1386 at step 1390 comprising a plurality of capture probes 1388 where the capture regions 1376, 1380 of the cleaved amplicons competitively hybridize to capture probes 1388.

In the embodiments of FIGS. 10-13, the cleavage amplicons introduced to the array do not include any portion of the target genomic region or a sequence complementary thereof. The capture regions are used in association with different target genomic regions, and the labeled oligonucleotide is used to differentiate between regions. In this manner, the cleaved amplicons competitively hybridize to common capture probes, and the quantitation of the target genomic regions is determined by the detected labels corresponding to cleaved products that bind to the array.

As described previously, the embodiments of the present invention shown in FIGS. 2-13 depict two separate fixed sequence oligonucleotides used to interrogate each locus or allele. However, in some aspects, however, a single probe can be used which comprises two or more distinct non-adjacent fixed sequence oligonucleotides that are complementary to the loci including precircle probes. Such precircle probes are described, e.g., by Lizardi in U.S. Pat. Nos. 5,854,033 and 6,316,229, and can be linearized prior to hybridization to the array by, e.g., including a site for a restriction endonuclease in the probe.

Universal Amplification

In certain aspects of the invention, universal amplification is used to amplify the ligation products following hybridization and ligation of the fixed sequence oligonucleotides, either directly or following extension or the introduction of a bridging oligonucleotide. In a multiplexed assay system, amplification preferably is done through universal amplification using universal primers that hybridize to universal primer regions on the first and second fixed sequence oligonucleotide of each set. The universal primer regions from the fixed sequence oligonucleotides become a part of the ligation products, where the ligation products can then be amplified in a single universal amplification reaction. Although these universal primer sequences preferably are introduced via the fixed sequence oligonucleotides, they may also be added to the proximal ends of the ligation products via ligation. The introduction of universal primer regions to the fixed sequence oligonucleotides allows a subsequent controlled universal amplification of all or a portion of the ligation products prior to array hybridization. The amplicon produced from this amplification process can be used directly or further processed prior to introduction to the array for detection. In specific embodiments, the amplicon is cleaved, and the portion comprising the capture region is introduced to the array for hybridization and detection. Bias and variability can be introduced during DNA amplification, such as that seen during polymerase chain reaction (PCR). In cases where an amplification reaction is multiplexed, there is the potential that loci will amplify at different rates or efficiency. Sets of primers for a given locus may behave differently based on sequence context of the primer and template DNA, buffer conditions, and other conditions. In certain aspects, the universal primer regions used in the methods are designed to be compatible with conventional multiplexed assay methods that utilize general priming mechanisms to analyze large numbers of nucleic acids simultaneously. Such "universal" priming methods allow for efficient, high volume analysis of the quantity of nucleic acid regions present in a genetic sample, and allow for comprehensive quantification of the presence of nucleic acid regions within such a sample.

The entirety of a ligation reaction or an aliquot of the ligation reaction may be used for universal amplification. Using an aliquot allows parallel amplification reactions to be undertaken using the same or different conditions (e.g., polymerase, buffers, and the like), e.g., to ensure that bias is not inadvertently introduced due to experimental conditions. In addition, variations in primer concentrations may be used to effectively limit the number of sequence specific amplification cycles. Examples of multiplexing assay methods include, but are not limited to, those described in Oliphant et al., U.S. Pat. No. 7,582,420.

As described in detail herein, many methods of the invention utilize coupled reactions for multiplex detection where oligonucleotides from an early phase of the multi-step process contain sequences that may be used in a later phase of the process. Processes known in the art for amplifying and/or detecting nucleic acids in samples can be used, alone or in combination, including but not limited to the methods described below. In certain aspects, the methods of the invention utilize one of the following combined selective and universal amplification techniques: (1) LDR coupled to PCR; (2) primary PCR coupled to secondary PCR coupled to LDR; and (3) primary PCR coupled to secondary PCR. Each of these combinations of techniques can utilize probe regions from an early phase in the process that may be used as a primer sequence in a later phase of the process.

Barany et al., U.S. Pat. Nos. 6,852,487, 6,797,470, 6,576,453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429,453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction with detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

The nucleic acid regions of interest are identified using hybridization techniques and arrays. Methods for conducting polynucleotide hybridization assays for detection are well-developed and well-known in the art. Hybridization assay procedures and conditions will vary depending on the application and are selected in accordance with the general binding methods known including those referred to in: Maniatis et al. Molecular Cloning: A Laboratory Manual ($2^{nd}$ Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

In some embodiments, the arrays comprise multiple substrates in solution, such as those taught, e.g., in U.S. Appln No. 20140057269 and U.S. Appln No. 20140042366 and U.S. Appln No. 20140024550.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964).

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Patent application 60/364,731 and in PCT Application PCT/US99/06097 (published as WO99/47964).

In certain aspects, the capture region of the ligation products from a single sample or the amplicons thereof contain index sequences that identify the ligation products as being from a particular sample. The features of the array will comprise capture probes that include sequences complementary to the index sequences of the different samples to allow identification of the loci from a particular sample from which the loci originated.

Estimation of Fetal DNA Proportion in a Maternal Sample

The proportion of fetal DNA in a maternal sample may be used as a part of the risk calculation of the present invention, as fetal proportion provides important information on the expected statistical presence of chromosomal dosage. Variation from the expected statistical presence may be indicative of fetal aneuploidy, an in particular a fetal trisomy or monosomy of a particular chromosome.

Any methods known in the art to estimate the percentage of fetal DNA in a maternal sample may be used, including quantifying Y sequences if the fetus is male or looking at epigenetic markers (see, e.g., Chim, et al., PNAS USA, 102:14753-58 (2005)). Using fetal proportion as one component of the risk calculation is particularly helpful in circumstances where the level of fetal DNA in a maternal sample is low. Further, knowledge of the fetal DNA percentage may be used to determine what if any additional analyses can be performed on the sample, as it may be the case at a certain lower bound of fetal DNA percentage a system is not able to reliably perform analysis. In other aspects, determining the fetal DNA proportion in a maternal sample may additionally affect the level of certainty or power in detecting a fetal aneuploidy.

Although the following methods are described for determination of a total proportion of fetal content in a maternal sample, the proportion can also be determined on a chromosome by chromosome basis. For instance frequency information for fetal chromosome 21 can be determined as compared to fetal chromosome 18. In another example, two or more chromosomes can be used in detecting a fetal proportion, e.g., frequency of loci on chromosomes 1 and 2 can be used. In certain aspects, the chromosome used for determining fetal proportion is the chromosome interrogated for possible aneuploidy. In another aspect, the chromosome (s) used for determining fetal proportion are specifically not the chromosome interrogated for possible aneuploidy.

The DNA from a fetus will have approximately 50% of its loci inherited from the mother and approximately 50% its loci inherited from the father. Determining which genetic loci are contributed to the fetus from non-maternal sources (informative loci) allows the estimation of fetal DNA proportion in a maternal sample, and thus provides information used to calculate statistically significant differences in chromosomal dosages for chromosomes of interest.

In certain aspects, determination of non-maternal polymorphisms is achieved through targeted SNP and/or mutation analysis to estimate the percentage of fetal DNA in a maternal sample—a process which is particularly adaptable to the array analysis of the present invention. The percent fetal cell free DNA in a maternal sample can be quantified using multiplexed SNP detection without prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploid, e.g., not chromosomes 21, 18, or 13. The selected polymorphic nucleic acid regions from the maternal sample (e.g., plasma) are amplified. In a preferred aspect, the amplification is universal; and in a preferred embodiment, the selected polymorphic nucleic acid regions are amplified in one reaction in one vessel, and in a preferred embodiment, the selected polymorphic nucleic acid regions are amplified in one reaction in one vessel with the ligation products of the fixed sequence oligonucleotides used to determine a chromosomal aneuploidy. Each allele of the selected polymorphic nucleic acid regions in the maternal sample is determined and quantified. In a preferred aspect, high throughput sequencing is used for such determination and quantification.

Loci are thus identified where the maternal and non-maternal genotypes are different; e.g., the maternal genotype is homozygous and the non-maternal genotype is heterozygous. This identification of informative loci is accomplished by observing a high frequency of one allele (>80%) and a low frequency (<20% and >0.15%) of the other allele for a particular selected nucleic acid region. The use of multiple loci is particularly advantageous as it reduces the amount of variation in the measurement of the abundance of the alleles between loci. All or a subset of the loci that meet this requirement are used to determine fetal contribution through statistical analysis. In one aspect, fetal contribution is determined by summing the low frequency alleles from two or more loci together, dividing by the sum of the low and high frequency alleles and multiplying by two.

For many alleles, maternal and non-maternal sequences may be homozygous and identical, and as this information therefore does not distinguish between maternal and non-maternal DNA it is not useful in the determination of percent fetal DNA in a maternal sample. The present invention utilizes allelic information where there is a distinguishable difference between the non-maternal and maternal DNA (e.g., a fetal allele containing at least one allele that differs from the maternal allele) in calculations of percent fetal DNA. Data pertaining to allelic regions that are the same for maternal and non-maternal DNA are thus not selected for analysis, or are removed from the pertinent data prior to estimation of the fetal DNA proportion so as not to mask the useful data. Additional exemplary processes for quantifying fetal DNA in maternal plasma can be found, e.g., in Chu, et al., Prenat. Diagn., 30:1226-29 (2010), which is incorporated herein by reference.

Data Analysis

Once percent fetal cell free DNA has been calculated, this data may be combined with methods for aneuploidy detection to determine the likelihood that a fetus may contain an aneuploidy. In one aspect, an aneuploidy detection method that utilizes analysis of random DNA segments is used, such as that described in, e.g., Quake, U.S. Ser. No. 11/701,686; and Shoemaker et al., U.S. Ser. No. 12/230,628. In a preferred aspect, aneuploidy detection methods that utilize analysis of selected nucleic acid regions are used. In this aspect, the percent fetal cell free DNA for a sample is calculated. The chromosomal ratio for that sample, a chromosomal ratio for the normal population and a variation for the chromosomal ratio for the normal population is determined, as described herein. Alternatively, the calculated chromosomal ration uses an expectation for a chromosomally normal sample and an expectation for an aneuploid sample. The calculated chromosomal ratio for a sample is then compared to those expectations.

In one preferred aspect, the chromosomal ratio and its variation for the normal population are determined from normal samples that have a similar percentage of fetal DNA. An expected aneuploid chromosomal ratio for a DNA sample with that percent fetal cell free DNA is calculated by adding the percent contribution from the aneuploid chromosome. The chromosomal ratio for the sample may then be compared to the chromosomal ratio for the normal population and to the expected aneuploid chromosomal ratio to determine statistically, using the variation of the chromosomal ratio, if the sample is more likely normal or aneuploid, and the statistical probability that it is one or the other.

In a preferred aspect, the selected regions of a maternal sample include both regions for estimation of fetal DNA content as well as non-polymorphic regions from two or more chromosomes to detect a fetal aneuploidy in a single reaction. The single reaction helps to minimize the risk of contamination or bias that may be introduced during various steps in the assay system which may otherwise skew results when utilizing fetal DNA content to help determine the presence or absence of a chromosomal abnormality.

In other aspects, a selected nucleic acid region or regions may be utilized both for estimation of fetal DNA content as well as detection of fetal chromosomal abnormalities. The alleles for selected nucleic acid regions can be used to estimate fetal DNA content and these same selected nucleic acid regions can then be used to detect fetal chromosomal abnormalities ignoring the allelic information. Utilizing the same selected nucleic acid regions for both fetal DNA content and detection of chromosomal abnormalities may further help minimize any bias due to experimental error or contamination.

In one embodiment, fetal source contribution in a maternal sample regardless of fetal gender is measured using autosomal SNPs (see, Sparks, et al., Am. J. Obstet & Gyn., 206:319.e1-9 (2012)). The processes utilized do not require prior knowledge of paternal genotype, as the non-maternal alleles are identified during the methods without regard to knowledge of paternal inheritance. A maximum likelihood estimate using the binomial distribution may be used to calculate the estimated fetal nucleic acid contribution across several informative loci in each maternal sample. The processes for calculation of fetal acid contribution used are described, for example, in US Pub. No. 2013/0024127. The polymorphic regions used for determination of fetal contribution may be from chromosomes 1-12, and preferably do not target the blood group antigens. The estimate of fetal contribution from the polymorphic assays is used to define expected response magnitudes when a test chromosome is trisomic, which informs the statistical testing. The test statistic may consist of two components: a measure of deviation from the expected proportion when the sample is disomic; and a measure of deviation from the expected proportion when the sample is trisomic. Each component is in the form of a Wald statistic (e.g., Harrell, Regression modeling strategies, (2001, Springer-Verlag), Sections 9.2.2 and 10.5) which compares an observed proportion to an expected proportion and divides by the variation of the observation.

The statistic Wj may be used to measure the deviation from expectation when the sample j is disomic, and is defined as $$W_j = \frac{p_j - p_0}{\sigma_{p_j}},$$

where pj and p0 are defined as described supra with the Z statistic, and $\sigma_{p_j}$ is the standard deviation of the observed proportion of representation for a given chromosome of interest. The standard deviation may be estimated using parametric bootstrap sampling to create a distribution of pj proportions based on the mean counts and standard errors for our chromosomes of interest. The second statistic is $\hat{W}_j$, which replaces p0 with the fetal fraction adjusted reference proportion $\hat{p}_j$ is defined as $$\hat{p}_j = \frac{(1 + 0.5 f_j) p_0}{((1 + 0.5 f_j) p_0)(1 - p_0)},$$

where $f_j$ is the fetal fraction for sample j and $p_0$ is the reference proportion as before. This adjustment accounts for the increased representation of a test chromosome when the fetus was trisomic. Because this variance of counts across many loci is measured as a natural result of using multiple non-polymorphic assays for there test chromosomes, all estimates are taken within a nascent data set and do not require external reference samples or historical information with normalizing adjustments to control for process drift as is typically required for variance around the expected proportion.

The final statistic used was $S_j = W_j + \hat{W}_j$. Conceptually, deviations from disomic expectation and trisomic expectation are simultaneously evaluated and summarized into this single statistic. The particular advantage of combining these two indicators is that while deviation from disomy might be high, it may not reach the deviation expected for trisomy at a particular fetal contribution level. The $\hat{W}_j$ component will be negative in this case, in effect penalizing the deviation from disomy. An $S_j = 0$ indicated an equal chance of being disomic vs. trisomic.

Computer Implementation of the Processes of the Invention

According to an exemplary embodiment, a computer executes a software component that calculates fetal proportion and applies this information to the values of the dosage of genomic regions and/or chromosomes. In one embodiment, the computer may comprise a personal computer, but the computer may comprise any type of machine that includes at least one processor and memory.

The output of the software component comprises a report with a value of probability that a genomic region and/or a chromosome has a dosage abnormality. In a preferred aspect this report is an odds ratio of a value of the likelihood that a region or chromosome has two copies (e.g., is disomic) and a value of the likelihood that a region or chromosome has more copies (e.g., is trisomic) or less copies (e.g., is monosomic) copies. The report may be paper that is printed out, or electronic, which may be displayed on a monitor and/or communicated electronically to users via e-mail, FTP, text messaging, posted on a server, and the like.

Although the normalization process of the invention is shown as being implemented as software, it can also be implemented as a combination of hardware and software. In addition, the software for normalization may be implemented as multiple components operating on the same or different computers.

Both the server and the computer may include hardware components of typical computing devices, including a processor, input devices (e.g., keyboard, pointing device, microphone for voice commands, buttons, touchscreen, etc.), and output devices (e.g., a display device, speakers, and the like). The server and computer may include computer-readable media, e.g., memory and storage devices (e.g., flash memory, hard drive, optical disk drive, magnetic disk drive, and the like) containing computer instructions that implement the functionality disclosed when executed by the processor. The server and the computer may further include wired or wireless network communication interfaces for communication.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Subjects

A total of 878 maternal venous blood samples were analyzed with the following classification of trisomy status: 691 were disomic, 18 were trisomy 13, 37 were trisomy 18, and 132 were trisomy 21. The blood samples were obtained from pregnant women at least 18 years old with singleton pregnancies at 10-34 weeks' gestation. The trisomy classification had previously been determined for all samples tested; 486 samples were originally tested using the Harmony Prenatal Test from Ariosa Diagnostics, Inc. (San Jose, Calif.), and 396 samples were sourced from patients who underwent either amniotic diagnostic karyotyping or postnatal newborn examination followed by karyotyping when trisomy was suspected.

Example 2

Sample Preparation

Sample preparation and analysis was performed as described in Sparks, et al., Am J. Obstet Gynecol., 207(5): 374.e1-6 (2012). Cell-free DNA was purified from the plasma of each patient and DANSR™ (Digital Analysis of Selected Regions) assay products (e.g., tandem ligation products) were made from loci on chromosomes 13, 18, and 21. For this analysis, ligation assays using sets of fixed sequence oligonucleotides and bridging oligonucleotides corresponding to 864 genomic regions on each of chromosomes 13, 18, and 21 were used. The DNA sample was attached to a solid support and unhybridized oligonucleotides were removed prior to ligation. In addition, ligation assays using sets of fixed sequence oligonucleotides and bridging oligonucleotides corresponding to 576 polymorphic sites on chromosomes 1 through 12 were developed to evaluate the fraction of fetal cfDNA in each sample. A portion of the ligation assay product produced from each sample was amplified using universal primers and sequenced and the remaining portion of the ligation assay product was hybridized to a custom manufactured DNA array. Prior to hybridization, the amplicons were cleaved. These portions contained identical products.

Example 3

Ligation Product Quantification Using Arrays

Custom DNA arrays were manufactured by Affymetrix, Inc. (Santa Clara, Calif.) to specifically quantify products of the DANSR assay. DNA arrays were imaged on an Affymetrix GeneTitan® Multi-Channel (MC) Instrument. Each patient sample was assayed on a single custom DNA array. DNA arrays were manufactured and processed in interconnected sets of 384. Next generation sequencing data was produced on an Illumina HiSeq® 2500 (San Diego, Calif.). Clusters were generated on an Illumina Cluster Station using TruSeq™ Cluster Generation reagents (San Diego, Calif.). On average 1104 sequencing counts per assay were obtained.

Example 4

Data Analysis

A previously published algorithm entitled Fetal-Fraction Optimized Risk of Trisomy Evaluation (FORTE™), was used to assign risk scores (see, e.g., Sparks, et al., Am J. Obstet Gynecol., 207(5):374.e1-6 (2012)). Non-polymorphic ligation assays on chromosomes 13, 18, and 21 were used to determine chromosome proportion for each of these chromosomes. Polymorphic ligation assays were used to ascertain fetal fraction. Assay variability was defined as the coefficient of variation (CV) of sequence counts (sequencing) or intensities (DNA arrays) of an assay across samples; lower assay variability is preferred. Fetal fraction variability is defined as the relative standard-error of the measured fetal fraction.

Example 5

Results

For the 878 plasma samples assayed for trisomy risk there was complete concordance between array-based risk scores and trisomy status using the ligation assays and detection by hybridization. In contrast, the concordance between sequence-based risk scores and trisomy status was 99.6%. Sequencing reported high risk scores for two samples that had received low risk scores in a previous NIPT screen. These data demonstrate that trisomy risk scores were accurately obtained from array-based analysis.

Figure 14:
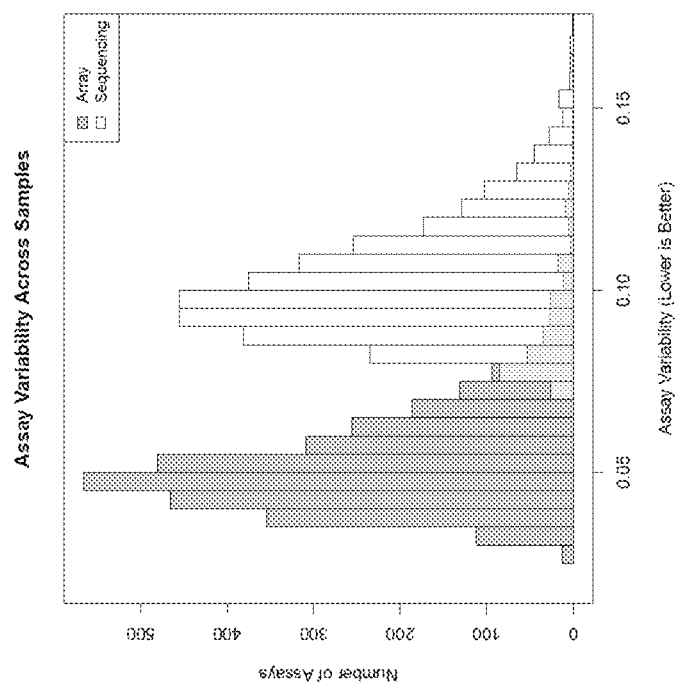
FIG. 14 shows the distribution of assay variability across samples for arrays and next generation sequencing.

In addition, array data decreases the assay variability by approximately two-fold. Accuracy, as measured by decreasing assay variability, was enhanced for array-based hybridization analysis compared to sequencing-based analysis. The median assay variability for array sequence detection showed a nearly two-fold improvement over next-generation-sequencing-based detection (0.051 versus 0.099; p-value<0.0001) (See FIG. 14). The bars of the histogram show the number of ligation assays (y-axis) that share a specific range of assay variability (x-axis). Array data is plotted in dark gray, sequencing data is plotted in white. Where the two populations of data overlap, the bars are light gray. The array-based quantified ligation products have significantly lower assay variability, where lower assay variability is better.

Arrays can be utilized to lower fetal fraction variability: The fraction of fetal DNA in plasma impacts the accuracy of the testing. The methods of the present invention measures, reports, and leverages fetal fraction using the FORTE algorithm to provide highly sensitive results with a low false positive rate (Sparks, et al., Am J Obstet Gynecol., 206(4): 319.e1-9 (2012)). FORTE calculated fetal fractions are extremely reproducible between array-based and sequencing-based analysis data ($R^2>0.99$). Because the array is able to simultaneously measure a larger number of ligation assays than multiplexed sequencing, fetal fraction estimates using array-based analysis are more precise with a median relative standard error of 0.013 compared to 0.021.

The data presented in the Examples show that two key sources of data variability are lower for arrays compared to next generation sequencing: 1) variation of the measured fetal fraction using polymorphic assays (fetal fraction variability) and 2) the variation of non-polymorphic assays across samples (assay variability). By including more polymorphic assays, an array-based ligation product prenatal test has been engineered that provides lower fetal-fraction variability resulting in better precision. By lowering assay variability, smaller aneuploidy changes can be measured, such as the smaller changes observed in low fetal fraction samples. The data demonstrates that the array platform is capable of reliable aneuploidy assessment. Moreover, array imaging is a rapid process and the turnaround time for sample quantitation is reduced to less than a minute per sample. The specific detection system employed in these Examples (GENETITAN™ Multi-Channel Instrument) can image >90 arrays per machine-hour. In contrast, even when samples are multiplexed in groups of 96 samples per lane, the HISEQ™ 2500 sequencing system has a throughput of 15 samples per machine-hour. This decrease in machine time and complexity translates directly to reductions in capital costs when array sequence detection is used.

The sequence based analysis leverages sample multiplexing in order to achieve economically efficient use of available sequence capacity. However, without normalization, a single sample can consume the majority of sequence reads in a flow-cell, reducing the reads available for determining trisomy risk in the remaining samples. In order to multiplex samples accurately, laborious and expensive processes to normalize quantities of input DNA are required. Even when efforts are made to equalize sample input, as was reported in a recent study, a four-fold variation in the median reads per-sample was observed for a 12-plex reaction (Jensen, et al., PLoS ONe, 8(3):e57381 (July 2014). Array-based NIPT approaches require no sample multiplexing. Instead, each sample is hybridized individually to a single array. Processing throughput is enhanced by physically connecting, e.g., 384 arrays onto a single multi-array plate for convenient high throughput handling. Because each sample is handled individually, time is saved and cost is reduced.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. An assay method for providing a statistical likelihood of a fetal copy number variation comprising:
providing a maternal plasma or serum sample comprising maternal and fetal cell free DNA;
interrogating at least 48 non-polymorphic loci from a first target genomic region by hybridizing sets of at least two fixed sequence oligonucleotides comprising a region complementary to a locus in the first target genomic region, wherein one of the fixed sequence oligonucleotides of each set comprises a first capture region, a first label binding region, and two restriction sites;
interrogating at least 48 non-polymorphic loci from a second target genomic region by hybridizing sets of at least two fixed sequence oligonucleotides comprising a region complementary to a locus in the second target genomic region, wherein one of the fixed sequence oligonucleotides of each set comprises the first capture region, a second label binding region, and two restriction sites;
ligating the hybridized fixed sequence oligonucleotides;
amplifying the ligated fixed sequence oligonucleotides to create amplicons;
cleaving the amplicons at the restriction sites to create cleaved amplicons, wherein each cleaved amplicon comprises the first capture region and the first or second label binding region;
detecting the cleaved amplicons from the first and second target genomic regions via hybridization of the first capture regions of the cleaved amplicons to an array comprising capture probes complementary to the first capture regions, wherein the cleaved amplicons from the first and second target genomic regions hybridize competitively to the capture probes complementary to the first capture regions;
quantifying the capture regions of the cleaved amplicons to determine a relative frequency of the interrogated non-polymorphic loci from the first and second target genomic regions by detecting the first and second label binding regions;
estimating the relative frequency of the first and second target genomic regions based on the determined relative frequency of the first and second label binding regions;
interrogating at least 48 polymorphic loci from at least one target genomic region different from the first and second target genomic regions by hybridizing sets of at least three fixed sequence allele-specific oligonucleotides for each polymorphic locus, wherein two of the at least three allele-specific oligonucleotides of each set comprises a sequence complementary to one allele at a polymorphic locus, a capture region specific for each polymorphic locus, a different label binding region for each allele at the polymorphic locus, and two restriction sites;
ligating the hybridized fixed sequence allele-specific oligonucleotides;
amplifying the ligated fixed sequence allele-specific oligonucleotides to create allele-specific amplicons;
cleaving the allele-specific amplicons at the restriction sites to create cleaved allele-specific amplicons, wherein each cleaved allele-specific amplicon comprises a polymorphic locus-specific capture region and an allele-specific label binding region;
detecting the cleaved allele-specific amplicons from the polymorphic loci via competitive hybridization of the polymorphic locus-specific capture regions of the cleaved allele-specific amplicons to capture regions on the array;
quantifying the alleles of the polymorphic loci by detecting the allele-specific label binding regions for each allele on the cleaved allele-specific amplicons to determine the fraction of fetal DNA in the sample;
determining the fraction of fetal DNA; and
calculating a statistical likelihood of a fetal copy number variation in the maternal sample using the estimated relative frequency of the first and second target genomic regions in the sample and the fraction of fetal DNA.

2. The assay method of claim 1, wherein three or more fixed sequence oligonucleotides for each set are used to interrogate each non-polymorphic locus in the first and second target genomic regions.

3. The assay method of claim 1, wherein each amplifying step uses universal amplification through a polymerase chain reaction.

4. The assay method of claim 1, further comprising:
identifying low frequency alleles from the quantified alleles of the polymorphic loci where the maternal DNA is homozygous and the fetal DNA is heterozygous; and
using the low frequency alleles from the polymorphic loci to determine the fraction of fetal DNA.

5. The assay method of claim 1, wherein the first genomic region is a chromosome.

6. The assay method of claim 1, wherein the second genomic region is a chromosome.

7. The assay method claim 1, wherein the first genomic region is a sub-chromosomal region.

8. The assay method claim 1, wherein the second genomic region is a sub-chromosomal region.

9. The assay method of claim 1, wherein the label binding regions of the fixed sequence oligonucleotides each comprise a label, wherein the first label binding regions each comprise a first label, and the second label binding regions each comprise a second label.

10. The assay method of claim 1, wherein the label binding regions of the fixed sequence oligonucleotides each comprise a sequence complementary to an oligonucleotide comprising a label, wherein the first label binding regions each comprise a sequence complementary to a first oligonucleotide comprising a first label, and the second label binding regions each comprise a sequence complementary to a second oligonucleotide comprising a second label.

11. An assay method for determining a likelihood of a fetal aneuploidy comprising the steps of:
providing a maternal plasma or serum sample comprising maternal and fetal cell free DNA;
introducing at least fifty first sets of two or more fixed sequence oligonucleotides complementary to a non-polymorphic locus in a first target genomic region in the maternal sample under conditions that allow a complementary region of each fixed sequence oligonucleotide to specifically hybridize to the non-polymorphic locus, wherein at least one of the fixed sequence oligonucleotides of each set comprises a universal primer site, a first capture region, a first label binding region, and two restriction sites;
introducing at least fifty second sets of two or more fixed sequence oligonucleotides complementary to a non-polymorphic locus in a second target genomic region in the maternal sample under conditions that allow a complementary region of each fixed sequence oligonucleotide to specifically hybridize to the non-polymorphic locus, wherein at least one of the fixed sequence oligonucleotides of each set comprises a universal primer site, the first capture region, a second label binding region, and two restriction sites;
introducing at least fifty third sets of three or more fixed sequence oligonucleotides complementary to a set of polymorphic loci in the maternal sample under conditions that allow a complementary region of each fixed sequence oligonucleotide to specifically hybridize to a polymorphic locus, wherein at least two of the three fixed sequence oligonucleotides of each set comprises a universal primer site, a sequence complementary to one allele at a polymorphic locus, an allele-specific label binding region for each allele at the polymorphic locus, two restriction sites, and a polymorphic locus-specific capture region, wherein the capture region for each polymorphic locus is different from the capture region for every other polymorphic locus and different from the first capture region;
hybridizing the first, second and third sets of fixed sequence oligonucleotides to the first and second target genomic regions and the polymorphic loci;
extending at least one of the hybridized fixed sequence oligonucleotides of the first, second and third sets to form adjacently hybridized fixed sequence oligonucleotides;
ligating the hybridized fixed sequence oligonucleotides of the first, second and third sets to create ligation products;
amplifying the ligation products using the universal primer sites to create amplicons corresponding to the polymorphic loci;
cleaving the amplicons at the restriction sites to create cleaved amplicons, wherein each cleaved amplicon comprises one capture region and one label binding region;
applying the cleaved amplicons to an array, wherein the array comprises first capture probes complementary to the first capture regions on the cleaved amplicons from the first and second target genomic regions, and wherein the array comprises capture probes complementary to the capture regions on the cleaved amplicons from each polymorphic locus;
hybridizing the first capture regions of the cleaved amplicons from the first and second target genomic regions to first capture probes on an array;
hybridizing the capture regions of the cleaved amplicons from the polymorphic loci to capture probes on the array;
detecting the hybridized cleaved amplicons;
quantifying a relative frequency of the cleaved amplicons corresponding to loci from the first target genomic region and a relative frequency of the cleaved amplicons corresponding to loci from the second target genomic region by detecting the first and second label binding regions;
quantifying a relative frequency of each allele from the polymorphic loci by detecting the allele-specific label binding regions for each allele on the cleaved amplicons to determine a percent fetal cell free DNA; and
computing a likelihood of fetal aneuploidy using the relative frequency of the cleaved amplicons corresponding to loci from the first and second target genomic regions to determine the likelihood of a fetal aneuploidy and the determined percent fetal cell free DNA.

12. The assay method of claim 11, wherein the relative frequencies of the cleaved amplicons corresponding to the loci from the first target genomic region are summed and the relative frequencies of the cleaved amplicons corresponding to the loci from the second target genomic region are summed, and the sum from the cleaved amplicons corresponding to the loci from the first target genomic region are compared to the sum from the cleaved amplicons corresponding to the loci from the second target genomic region to calculate a target genomic region ratio.

13. The assay method of claim 11, wherein a single hybridized fixed sequence oligonucleotide of each set is extended to form adjacently hybridized fixed sequence oligonucleotides.

14. The assay method of claim 11, wherein the label binding regions of the fixed sequence oligonucleotides each comprise a label, wherein the first label binding regions each comprise a first label, and the second label binding regions each comprise a second label.

15. The assay method of claim 11, wherein the label binding regions of the fixed sequence oligonucleotides each comprise a sequence complementary to an oligonucleotide comprising a label, wherein the first label binding regions each comprise a sequence complementary to a first oligonucleotide comprising a first label, and the second label binding regions each comprise a sequence complementary to a second oligonucleotide comprising a second label.

16. An assay method for determining a likelihood of a fetal aneuploidy comprising the steps of:
  providing a maternal plasma or serum sample comprising maternal and fetal cell free DNA;
  introducing at least fifty first sets of two or more fixed sequence oligonucleotides complementary to a set of non-polymorphic loci in a first target genomic region in the maternal sample under conditions that allow a complementary region of each fixed sequence oligonucleotide to specifically hybridize to the non-polymorphic loci, wherein at least one of the fixed sequence oligonucleotides of each set comprises a universal primer site, a first capture region, a first label binding region, and two restriction sites;
  introducing at least fifty second sets of two or more fixed sequence oligonucleotides complementary to a set of non-polymorphic loci in a second target genomic region in the maternal sample under conditions that allow a complementary region of each fixed sequence oligonucleotide to specifically hybridize to the non-polymorphic loci, wherein at least one of the fixed sequence oligonucleotides of each set comprises a universal primer site, a first capture region, a second label binding region, and two restriction sites;
  introducing two or more third sets of three or more fixed sequence oligonucleotides complementary to a set of polymorphic loci in the maternal sample under conditions that allow a complementary region of each fixed sequence oligonucleotide to specifically hybridize to a polymorphic locus, wherein at least two of the three or more fixed sequence oligonucleotides of each set comprises a universal primer site, a sequence complementary to one allele at the polymorphic locus, an allele-specific label binding region for each allele at the polymorphic locus, two restriction sites, and a polymorphic locus-specific capture region, wherein the capture region for each polymorphic locus is different from the capture region for every other polymorphic locus and different from the first capture region;
  hybridizing the first, second and third sets of fixed sequence oligonucleotides to the first and second target genomic regions and polymorphic loci;
  extending at least one of the hybridized fixed sequence oligonucleotides of the first, second and third sets to form adjacently hybridized fixed sequence oligonucleotides for each set;
  ligating the adjacently hybridized fixed sequence oligonucleotides from the first, second and third sets to create ligation products;
  amplifying the ligation products using the universal primer sites to create amplicons;
  cleaving the amplicons at the restriction sites to create cleaved amplicons, wherein each cleaved amplicon comprises one capture region and one label binding region;
  applying the cleaved amplicons to an array, wherein the array comprises first capture probes complementary to the first capture regions on the cleaved amplicons from the first and second target genomic regions, and wherein the array comprises capture probes complementary to the capture regions on the cleaved amplicons from each polymorphic locus;
  hybridizing the first capture regions of the cleaved amplicons from the first and second target genomic regions to first capture probes on an array;
  hybridizing the capture regions of the cleaved amplicons from the polymorphic loci to capture probes on the array;
  detecting the hybridized cleaved amplicons;
  quantifying a relative frequency of each allele from the polymorphic loci by detecting the allele-specific label binding regions for each allele on the cleaved amplicons to determine a percent fetal cell free DNA;
  determining the percent of fetal cell free DNA by identifying low frequency alleles from the quantified alleles where a maternal locus is homozygous and a corresponding fetal locus is heterozygous;
  quantifying a relative frequency of cleaved amplicons corresponding to loci from the first target genomic region and a relative frequency of cleaved amplicons corresponding to loci from the second target genomic region by detecting the first and second label binding regions; and
  computing a likelihood of a fetal aneuploidy using the relative frequency of cleaved amplicons corresponding to loci from the first and second target genomic regions and the percent fetal cell free DNA.

17. The assay method of claim 16, further comprising comparing the relative frequencies of the cleaved amplicons corresponding to loci from the first and second target genomic regions and adjusting the likelihood of a fetal aneuploidy based on the percent fetal cell-free DNA.

18. The assay method of claim 16 wherein the relative frequencies of the cleaved amplicons corresponding to the loci from the first target genomic region are summed and the relative frequencies of the cleaved amplicons corresponding to the loci from the second target genomic region are summed, and the sum from the cleaved amplicons corresponding to the loci from the first target genomic region are compared to the sum from the cleaved amplicons corresponding to the loci from the second target genomic region to calculate a target genomic region ratio.

19. The assay method of claim 16, wherein the polymorphic loci are autosomal loci.

20. The assay method of claim 16, wherein one or more corresponding fetal polymorphic loci comprise more than one genetic variation as compared to a maternal locus.

21. The assay method of claim 16, wherein the cleaved amplicons from loci of the first and second target genomic regions and the cleaved amplicons from the polymorphic loci are created in a single vessel.

22. The assay method of claim 16, wherein the label binding regions of the fixed sequence oligonucleotides each comprise a label, wherein the first label binding regions each comprise a first label, and the second label binding regions each comprise a second label.

23. The assay method of claim 16, wherein the label binding regions of the fixed sequence oligonucleotides each comprise a sequence complementary to an oligonucleotide comprising a label, wherein the first label binding regions each comprise a sequence complementary to a first oligonucleotide comprising a first label, and the second label binding regions each comprise a sequence complementary to a second oligonucleotide comprising a second label.

* * * * *